United States Patent
Armani et al.

(10) Patent No.: US 9,326,976 B2
(45) Date of Patent: May 3, 2016

(54) CARBAMATE DERIVATIVES

(71) Applicant: CHIESI FARMACEUTICI S.P.A., Parma (IT)

(72) Inventors: Elisabetta Armani, Parma (IT); Gabriele Amari, Parma (IT); Carmelida Capaldi, Parma (IT); Charles Baker-Glenn, Saffron Walden (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 14/723,924

(22) Filed: May 28, 2015

(65) Prior Publication Data

US 2015/0352090 A1    Dec. 10, 2015

(30) Foreign Application Priority Data

Jun. 5, 2014    (EP) .................................... 14171263

(51) Int. Cl.
*A61K 31/444* (2006.01)
*C07D 453/02* (2006.01)
*A61K 9/00* (2006.01)

(52) U.S. Cl.
CPC ............. *A61K 31/444* (2013.01); *A61K 9/0073* (2013.01); *C07D 453/02* (2013.01)

(58) Field of Classification Search
None
See application file for complete search history.

(56) References Cited

U.S. PATENT DOCUMENTS

| 9,090,606 B2 | 7/2015 | Armani et al. |
| 2013/0005716 A1* | 1/2013 | Armani ................ C07D 213/89 514/227.8 |
| 2014/0155373 A1 | 6/2014 | Armani et al. |
| 2014/0155427 A1 | 6/2014 | Armani et al. |
| 2015/0158857 A1 | 6/2015 | Amari et al. |
| 2015/0158858 A1 | 6/2015 | Amari et al. |

FOREIGN PATENT DOCUMENTS

| EP | 2 022 783 | 2/2009 |
| EP | 2 216 327 | 8/2010 |

OTHER PUBLICATIONS

European Search Report in Application No. 14171263.8 issued Sep. 2, 2014.
U.S. Appl. No. 14/723,964, filed May 28, 2015, Armani, et al.

* cited by examiner

*Primary Examiner* — Timothy R Rozof
(74) *Attorney, Agent, or Firm* — Oblon, McClelland, Maier & Neustadt, L.L.P.

(57) ABSTRACT

Compounds of formula (I) defined herein are both phosphodiesterase 4 (PDE4) enzyme inhibitors and muscarinic M3 receptor antagonists and are useful for the prevention and/or treatment of diseases of the respiratory tract.

13 Claims, No Drawings

CARBAMATE DERIVATIVES

CROSS REFERENCES TO RELATED APPLICATIONS

This application claims priority to European Patent Application No. 14171263.8, filed on Jun. 5, 2014, which is incorporated herein by reference in its entirety.

BACKGROUND OF THE INVENTION

1. Field of the Invention

The present invention relates to novel compounds which are both phosphodiesterase 4 (PDE4) enzyme inhibitors and muscarinic M3 receptor antagonists. The present invention also relates methods of preparing such a compound, compositions containing such a compound, and therapeutic uses of such a compound.

2. Discussion of the Background

Chronic obstructive pulmonary disease (COPD) is a respiratory disorder characterized by progressive, not fully reversible, airflow limitation associated with an abnormal pulmonary inflammatory response to noxious particles or gases.

For this reason, bronchial relaxation and inflammatory response suppression represent a mechanistic approach to the treatment of COPD that might improve symptoms such as dyspnea, wheezing, chest tightness, cough and mucus secretion, improve health status and reduce exacerbations.

Nowadays, the drug therapy options for COPD fall into two general classes: bronchodilators, (β2-adrenoceptor agonists, antimuscarinic agents and methylxanthines) and antiinflammatory agents (glucocorticosteroids and selective phosphodiesterase-4 (PDE4) inhibitors).

Bronchodilator drugs are the current mainstay of treatment for symptoms' relief.

As anticholinergic bronchodilators, the efficacy of muscarinic M3 antagonists is based on the fact that the major reversible component of airflow narrowing in COPD patients is the increase of acetylcholine (ACh) released to airway smooth muscle, by the bronchial postganglionic vagal efferent in some pathological conditions. Therefore, compounds that antagonize the action of ACh at muscarinic receptors are able to counteract the bronchoconstriction and thus improve lung function in these patients.

Muscarinic antagonists block the effects of ACh at muscarinic receptors. Currently, there are five known muscarinic receptor subtypes (M1-M5); human airway smooth muscle contains M1, M2, and M3 receptors. M1 receptors facilitate neurotransmission through parasympathetic ganglia and are weakly expressed on submucosal glands in human airways. The M2 receptors are located on the smooth-muscle fibers. Some studies have suggested a small role of M2 mediating the inhibition of airway smooth-muscle relaxation caused by adenylyl cyclase activation by compounds such as beta agonists. In addition, presynaptic M2 receptors are found on postganglionic parasympathetic nerves that project to airway smooth muscle and mucus-producing cells. These presynaptic M2 autoreceptors provide a negative feedback mechanism, which, when stimulated, inhibit further release of ACh. Postsynaptic M3 receptors are known to mediate both contraction of smooth muscle in the respiratory tract and mucus secretion, making them a major target for symptomatic relief of COPD. Consequently, in the airways, the major effects of muscarinic antagonists are bronchodilation and reduction of mucus secretion via blockage of ACh-induced effects in the parasympathetic nervous system.

Given the distribution of muscarinic receptors, systemically available agents that bind to muscarinic receptors outside of the respiratory tract have the potential to produce unwanted side effects such as tachycardia, dry mouth, urinary retention and constipation. Whereas dry mouth is the most common systemic anticholinergic side effect associated with the use of antimuscarinic antagonists as a result of the systemic blockade of M1 and M3 receptors, the most potentially serious systemic effect is tachycardia, which results from the blockade of cardiac M2 receptors.

Inhaled anticholinergic antimuscarinic drugs approved for the treatment of COPD include ipratropium bromide (Atrovent®), oxitropium bromide (Oxivent®), and tiotropium bromide (Spiriva®). Both ipratropium and oxitropium are short-acting agents. In contrast, tiotropium bromide is the only long-acting antimuscarinic agent (LAMA) currently marketed for COPD, proved to be suitable for once-daily administration as a dry powder. Several others newer LAMAs are newly registered for the treatment of COPD, including aclidinium bromide and glycopyrrolate bromide, or are currently in phase III development, including umeclidinium.

Although bronchodilators are quite effective to improve symptoms, they do not address the underlying chronic inflammation or the changes in airway structure.

Standard treatment with glucocorticosteroids as antiinflammatory agents has demonstrated limited efficacy. However, among the antiinflammatory agents currently being developed, PDE4 inhibitors proved to be effective in attenuating the responses of various inflammatory cells, through their ability to elevate cAMP levels.

PDE4 is the predominant PDE expressed in neutrophils and T cells, suggesting that PDE4 inhibitors would be effective in controlling inflammation in COPD. Inhibition of PDE4 in inflammatory cells influences various specific responses, such as the production and/or release of pro-inflammatory mediators including cytokines and reactive oxygen species, with a well-documented efficacy in animal models mimicking certain aspects of asthma and COPD, as well as inflammatory bowel disease, atopic dermatitis, psoriasis and rheumatoid arthritis.

The selective PDE4 inhibitor, roflumilast (Daxas®) is an approved phosphodiesterase-4 inhibitor for the treatment of COPD associated with chronic bronchitis and a history of exacerbations. Roflumilast inhibits lung inflammation and emphysema in a smoking model of COPD in mice. In COPD patients, oral roflumilast given over 4 weeks significantly reduces the numbers of neutrophils (by 36%) and CXCL8 concentrations in sputum. In clinical trials roflumilast (500 mg once daily) given over 12 months improved lung function in COPD patients to a small extent but had little effect in reducing exacerbations or improving quality of life. More recently roflumilast has been shown to significantly improve FEV 1 (by approximately 50 mL) and reduce exacerbation (by about 15%) in patients with severe disease who have frequent exacerbations and mucus hypersecretion. Roflumilast provides clinical benefit when added to salmeterol or tiotropium and so may be used as an additional treatment in patients with severe disease.

However, the clinical utility of PDE4 inhibitors has so far been compromised by the occurrence of mechanism-associated side effects, including headache, nausea and emesis, which often limited the maximally tolerated dose. This problem could be overcome by inhaled delivery and designing compounds with a potentially more advantageous therapeutic window.

Since bronchial relaxation and inflammatory response suppression represent a mechanistic approach to the treatment of COPD, the combination of muscarinic M3 antagonism with selective PDE4 inhibition may lead to a new class of drugs, combining both bronchodilating and antiinflammatory properties in one molecule, which may open new perspectives in the management of COPD.

SUMMARY OF THE INVENTION

Accordingly, it is one object of the present invention to provide novel compounds which act as both an inhibitor of the phosphodiesterase 4 (PDE4) enzyme and an muscarinic M3 receptor antagonist.

It is another object of the present invention to provide novel methods of preparing such a compound.

It is another object of the present invention to provide novel compositions which contain such a compound.

It is another object of the present invention to provide novel therapeutic uses of such a compound.

These and other objects, which will become apparent during the following detailed description, have been achieved by the inventors' discovery that compounds of formula (I), described below, act as both an inhibitor of the phosphodiesterase 4 (PDE4) enzyme and an muscarinic M3 receptor antagonist.

Thus, in one embodiment, the present invention provides compounds of formula (I):

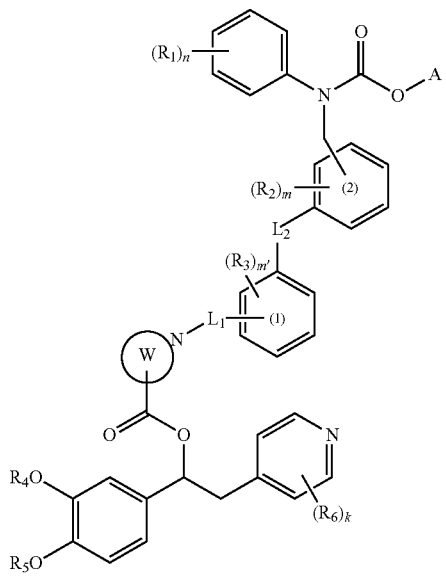

(I)

wherein
each $R_1$ is hydrogen or is independently selected in the group consisting of: halogen, $(C_1-C_4)$ alkyl, $(C_1-C_4)$ alkoxy, $(C_1-C_4)$ haloalkyl, hydroxy, $—SO_2NR^IR^{II}$, $—CN$, $—N(R^I)SO_2R^{III}$, $—NR^IR^{II}$, $—C(O)NR^IR^{II}$ and $—N(R^I)C(O)R^{III}$, and wherein said $(C_1-C_4)$ alkyl is optionally substituted by one or more groups selected from $(C_3-C_7)$ cycloalkyl, hydroxy and $—NR^IR^{II}$ and wherein said $(C_1-C_4)$ alkoxy is optionally substituted by one or more halogens or groups $(C_3-C_7)$ cycloalkyl wherein:
$R^I$ is hydrogen or $(C_1-C_6)$ alkyl;
$R^{II}$ is hydrogen or $(C_1-C_6)$ alkyl;
$R^{III}$ is hydrogen or $(C_1-C_6)$ alkyl;
n is an integer ranging from 1 to 3;

each $R_2$ and $R_3$ are different or the same and are independently selected from the group consisting of hydrogen, halogen, $(C_1-C_4)$ alkyl, $(C_1-C_4)$ alkoxy, $(C_1-C_4)$ haloalkyl, hydroxy, $—SO_2NR^IR^{II}$, $—CN$, $—N(R^I)SO_2R^{III}$, $—NR^IR^{II}$, $—C(O)NR^IR^{II}$ and $—N(R^I)C(O)R^{III}$ and wherein said $(C_1-C_4)$ alkyl is optionally substituted by one or more groups selected from $(C_3-C_7)$ cycloalkyl, hydroxy and $—NR^IR^{II}$ and wherein said $(C_1-C_4)$ alkoxy is optionally substituted by one or more halogens or groups $(C_3-C_7)$ cycloalkyl wherein:
$R^I$ is hydrogen or $(C_1-C_6)$ alkyl;
$R^{II}$ is hydrogen or $(C_1-C_6)$ alkyl;
$R^{III}$ is hydrogen or $(C_1-C_6)$ alkyl;
m and m' are different or the same and are an integer ranging from 1 to 3;
$R_4$ and $R_5$ are different or the same and are independently selected from the group consisting of
H;
$(C_3-C_7)$ cycloalkylcarbonyl;
$(C_1-C_6)$ alkyl, optionally substituted by one or more substituents selected from $(C_3-C_7)$ cycloalkyl and $(C_5-C_7)$ cycloalkenyl;
$(C_1-C_6)$ haloalkyl;
$(C_3-C_7)$ cycloalkyl;
$(C_5-C_7)$ cycloalkenyl;
$(C_2-C_6)$ alkenyl; and
$(C_2-C_6)$ alkynyl;
or $R_4$ and $R_5$ together with the interconnecting atoms, form a 2,2-difluoro-1,3-dioxolane ring of formula (r) fused to the phenyl moiety which bears groups $—OR_4$ and $—OR_5$, wherein asterisks indicate carbon atoms shared with such phenyl ring:

(r)

each $R_6$ is selected from the group consisting of CN, $NO_2$, $CF_3$ and halogen atoms;
k is 0 or an integer ranging from 1 to 3;
$L_1$ is selected from the list consisting of
a bond;
$—C(O)—$;
$—SO_2—$; and
$—(CH_2)—$;
the group

is selected from divalent saturated monocyclic heterocloalkylene, with at least one nitrogen atom, which is linked to the $L_1$ residue by one of its nitrogen atom;
$L_2$ is a group selected from
a bond;
[1]-$(CH_2)_q$-[2];
[1]-C(O)NH—$(CH_2)_q$—NH—C(O)-[2];
[1]-C(O)O—$(CH_2)_q$—O—C(O)-[2];
[1]-$(CH_2)_q$O-[2];
[1]-O$(CH_2)_q$-[2];

[1]-(CH$_2$)$_q$—O—C(O)-[2];
[1]-C(O)O—(CH$_2$)$_q$[2]-;
[1]-(CH$_2$)$_q$—NH—C(O)-[2]; and
[1]-C(O)NH—(CH$_2$)$_q$[2]-;

wherein q is an integer ranging from 1 to 4; and wherein [1] and [2] represent, respectively, the point of attachment of group L$_2$ to a carbon atom of the phenylene ring (1) and to a carbon atom of the phenylene ring (2);

A is a nitrogen containing group which may be selected from:
  a group (a) which is —(CH$_2$)$_s$—NR$_8$R$_9$ wherein s is an integer ranging from 1 to 4 and R$_8$ and R$_9$ are independently hydrogen or (C$_1$-C$_4$) alkyl; and
  a group (b) which is a saturated monocyclic, bicyclic or tricyclic heterocyclic ring system optionally substituted by one or two groups R$_{10}$ which are at each occurrence independently selected from (C$_1$-C$_4$) alkyl and benzyl;

their N-oxides on each of the nitrogen atoms, deuterated derivatives, and pharmaceutically acceptable salts, or solvates thereof.

The present invention further provides a N-oxide on the pyridine ring of a compound of formula (I) which is represented by the formula (IA):

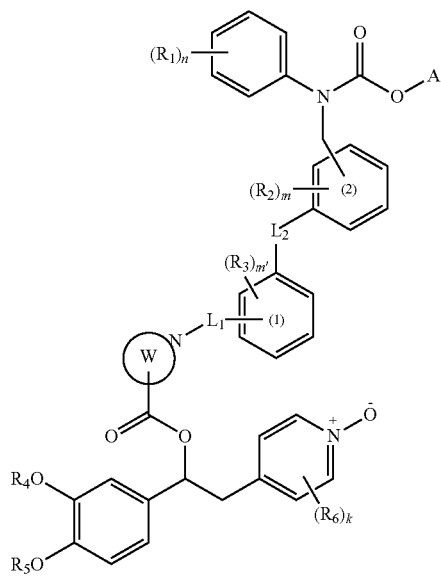

(IA)

wherein R$_1$, R$_2$, R$_3$, R$_4$, R$_5$, R$_6$, W, L$_1$, L$_2$, A, m, m', n and k are as described above.

The present invention further provides the corresponding deuterated derivatives of compounds of formula (I) wherein at least one hydrogen atom is substituted by corresponding atoms of deuterium.

The present invention also encompasses the pharmaceutically acceptable salts and/or solvates thereof.

The term "pharmaceutically acceptable salts" refers to derivatives of compounds of formula (I) or of their corresponding N-oxides on the pyridine ring wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic acid residues such as carboxylic groups.

Cations of inorganic bases which can be suitably used to prepare salts within the invention comprise ions of alkali or alkaline earth metals such as potassium, sodium, calcium or magnesium.

Salts obtained by reacting the main compound, functioning as a base, with an inorganic or organic acid to form a salt comprise, for example, salts of hydrochloric acid, hydrobromic acid, sulfuric acid, phosphoric acid, acetic acid, methane sulfonic acid, camphor sulfonic acid, oxalic acid, maleic acid, fumaric acid, succinic acid and citric acid.

The skilled person will appreciate that many organic compounds can form complexes with solvents in which they are reacted or from which they are precipitated or crystallized. These complexes are known as "solvates". Pharmaceutically acceptable solvates of compound of the invention are within the scope of the present invention.

Included within the scope of the present invention are also polymorphs and crystalline forms of compounds of formula (I), of their N-oxides on the pyridine ring, or of pharmaceutically acceptable salts, or solvates thereof.

Hereinafter, compounds of formula (I), (IA), (IB), (IC), (Ia), (Ib), (Ic), (Id) and (I)', corresponding N-oxides on the pyridine ring, enantiomers, diastereoisomers thereof, their pharmaceutically acceptable salts and solvates, and polymorphs or crystalline forms thereof defined in any aspect of the invention (except intermediate compounds described in the chemical processes) are referred to as "compounds of the invention".

The present invention further comprises a process for the preparation of compounds of the invention.

The present invention also provides pharmaceutical compositions of compounds of the invention either alone or in combination, in admixture with one or more pharmaceutically acceptable carriers.

In a further aspect the present invention provides the use of the compounds of the invention as a medicament.

In one aspect the present invention provides the use of the compounds of the invention for the manufacture of a medicament.

In particular the present invention provides the use of the compounds of the invention for the prevention and/or treatment of any disease wherein an inhibition of PDE4 activity along with muscarinic M3 receptor antagonism is desirable.

In particular the compounds of the invention alone or combined with other active ingredients may be administered for the prevention and/or treatment of a disease of the respiratory tract characterized by airway obstruction such as asthma and COPD. In one embodiment, the compounds of the invention may be administered for the prevention and/or treatment of COPD.

In a further aspect the present invention provides the use of compounds of the invention for the preparation of a medicament for the prevention and/or treatment of any disease wherein an inhibition of PDE4 activity along with muscarinic M3 receptor antagonism is desirable.

Moreover the present invention provides a method for prevention and/or treatment of any disease wherein an inhibition of PDE4 activity along with muscarinic M3 receptor antagonism is desirable, said method comprises administering to a patient in need of such treatment a therapeutically effective amount of a compound of the invention.

A further aspect of the present invention provides a suitable inhalation device, comprising a pharmaceutical composition of a compound of the invention, which may be respectively selected from a single- or multi-dose dry powder inhaler, a pressurized metered dosed inhaler or a nebulizer and in particular a soft mist nebulizer.

A further aspect of the present invention provides a kit comprising the pharmaceutical compositions of a compound of the invention either alone or in combination with one or more active ingredient and a device which may be a single- or multi-dose dry powder inhaler, a metered dose inhaler or a nebulizer.

DETAILED DESCRIPTION OF THE PREFERRED EMBODIMENTS

The term "halogen atoms" includes fluorine, chlorine, bromine, and iodine, preferably chlorine.

The term "$(C_1-C_x)$ alkyl" where x is an integer greater than 1, refers to straight-chained and branched alkyl groups wherein the number of constituent carbon atoms is in the range 1 to x. Particular alkyl groups are methyl, ethyl, n-propyl, i-propyl, n-butyl, sec-butyl, i-butyl, and t-butyl.

By analogy, the term "$(C_1-C_x)$ alkylene" represented also by the group —$(CH_2)_{1-x}$— refers to a divalent $(C_1-C_x)$alkyl radical, wherein $(C_1-C_x)$alkyl is as above defined.

The term "$(C_1-C_x)$ alkoxy" where x is an integer greater than 1 refers to straight-chained and branched alkoxy groups wherein the number of constituent carbon atoms is in the range 1 to x. Particular alkoxy groups are methoxy, ethoxy, n-propoxy, i-propoxy, n-butoxy, sec-butoxy, i-butoxy, and t-butoxy.

The expressions "$(C_1-C_x)$ haloalkyl" refer to the above defined "$(C_1-C_x)$alkyl" groups wherein one or more hydrogen atoms are replaced by one or more halogen atoms, which can be the same or different from each other. Examples of said $(C_1-C_6)$haloalkyl groups may thus include halogenated, polyhalogenated and fully halogenated alkyl groups wherein all of the hydrogen atoms are replaced by halogen atoms, e.g. trifluoromethyl or difluoro methyl groups.

The term "$(C_3-C_y)$ cycloalkyl", where y is an integer greater than or equal to 3, refers to saturated cyclic hydrocarbon groups containing from 3 to y ring carbon atoms. Examples include cyclopropyl, cyclobutyl, cyclopentyl, cyclohexyl, and cycloheptyl.

The expression "$(C_3-C_y)$cycloalkylcarbonyl" refers to $(C_3-C_y)$cycloalkyl-C(O)— groups wherein the group "$(C_3-C_y)$ cycloalkyl" has the meaning above defined and the group —C(O)— is a carbonyl group represented also by —C(=O)—.

The term "$(C_2-C_6)$alkenyl" refers to straight or branched, conjugated or non-conjugated, carbon chains with one or more double bonds, in cis or trans configuration, wherein the number of atoms is in the range 2 to 6.

The term "$(C_5-C_z)$ cycloalkenyl", where z is an integer greater than or equal to 5, refers to cyclic hydrocarbon groups containing from 5 to z ring carbon atoms and one or more double bonds.

The term "$(C_2-C_6)$alkynyl" refers to straight or branched carbon chains with one or more triple bonds wherein the number of atoms is in the range 2 to 6.

The expression "heterocycloalkyl" refers to monocyclic cycloalkyl groups with 3 to 6 ring atoms, in which at least one ring carbon atom is replaced by a heteroatom (e.g. N, NH, S or O). Non-limiting examples of heterocycloalkyl are represented by: pyrrolidinyl, thiazolidinyl, imidazolidinyl, oxazolidinyl, piperazinyl, piperidinyl, morpholinyl, thiomorpholinyl, and azetidinyl.

The expression "saturated monocyclic heterocycloalkylene" refers to divalent saturated monocyclic cycloalkyl groups with 3 to 6 ring atoms in which at least one ring carbon atom is replaced by a heteroatom selected for instance from N, NH, S or O. Non-limiting examples of "saturated monocyclic heterocycloalkylene" are represented by: pyrrolidinediyl, thiazolidinediyl, imidazolidinediyl, oxazolidinediyl piperazinediyl, piperidinediyl, morpholinediyl, thiomorpholinediyl, azetidinediyl radicals at any suitable position, and the like. Preferred "saturated monocyclic heterocycloalkylene" of the invention have 4 to 5 ring atoms, one heteroatom is a nitrogen atom, linked to the group $L_1$, the other heteroatom, when present, is S and are preferably represented by: azetidine-1,4-diyl tiazolidine-2,3-diyl, pyrrolidine-1,2-diyl, and imidazolidine-1,2-diyl.

The expression "heterocyclic ring system" refers to optionally substituted mono-, bi- or tri-cyclic ring systems which may be saturated, partially unsaturated or unsaturated, such as heterocycloalkyl or heteroaryl having 5 to 11 ring atoms in which at least one ring atom is a heteroatom (e.g. N, S or O). Examples of "heterocyclic ring system" are represented by: pyrrolidinyl, imidazolidinyl, piperazinyl, piperidinyl, quinuclidinyl, 8-azabicyclo[3.2.1]octanyl or dehydroxy scopine radical all optionally substituted by oxygen, $(C_1-C_x)$ alkyl or benzyl on a nitrogen atom.

As used in the present description an oxo moiety is represented by (O) as an alternative to the other common representation, e.g. (=O). Thus, in terms of general formula, the carbonyl group is herein preferably represented as —C(O)— as an alternative to the other common representations such as —CO—, —(CO)— or —C(=O)—. In general the bracketed group is a lateral group, not included into the chain, and brackets are used, when deemed useful, to help disambiguating linear chemical formulas; e.g. the sulfonyl group —$SO_2$— might be also represented as —$S(O)_2$— for clarity with respect to the sulfinic group —S(O)O—.

The present invention is directed to a class of compounds acting both as inhibitors of the phosphodiesterase 4 (PDE4) enzyme and as muscarinic M3 receptor antagonists.

The present invention relates to derivatives of general formula (I), N-oxides on the pyridine ring, deuterated derivatives and pharmaceutically acceptable salts or solvates thereof,

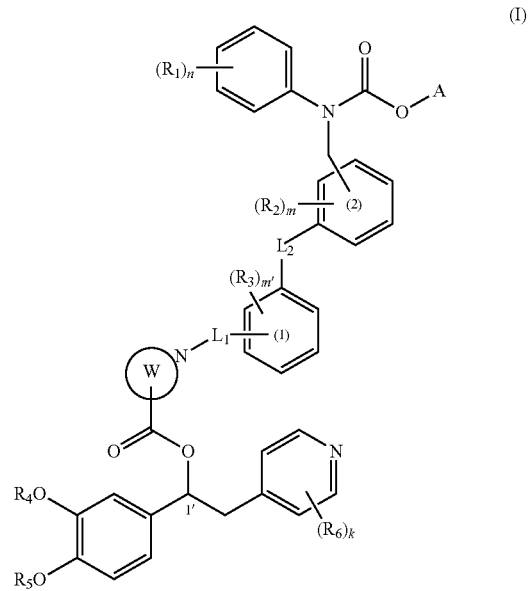

wherein $R_1, R_2, R_3, R_4, R_5, R_6, W, L_1, L_2, A, m, m', n$ and $k$ are as above defined.

Preferred compounds of formula (I) are those wherein the "saturated heterocyclic ring system" A is represented by a group of formula (i), (ii), (iii) or (iv):

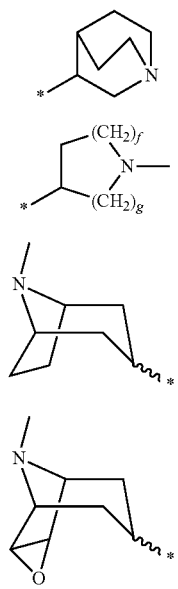

(i)

(ii)

(iii)

(iv)

wherein
f=1, 2 or 3;
g=1, 2 or 3.
and the asterisk (*) represents the point of attachment to the oxygen atom of formula (I).

More preferably A is represented by a group of formula (i) or (ii):

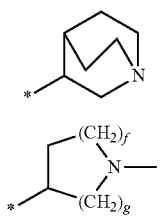

(i)

(ii)

wherein
f is 1, g is 2 and the asterisk (*) represents the point of attachment to the oxygen atom of formula (I).

It will be apparent to those skilled in the art that compounds of formula (I) at least contain one stereogenic center, namely represented by the carbon atom 1', and therefore exist as optical stereoisomers.

It will be apparent to the skilled person that compounds according to the invention may have at least two stereogenic centers, thus they may accordingly exist at least as four diastereoisomers. Where the compounds according to the invention possess more than two stereogenic centers, they will exist as $2^n$ diastereoisomers (wherein n here refers to the number of stereogenic centers). It is to be understood that all such isomers and mixtures thereof in any proportion are encompassed within the scope of the present invention.

In a preferred embodiment, the present invention is directed to compounds of formula (I)', which are compounds of formula (I) as above defined where the absolute configuration of carbon 1' is that shown herebelow:

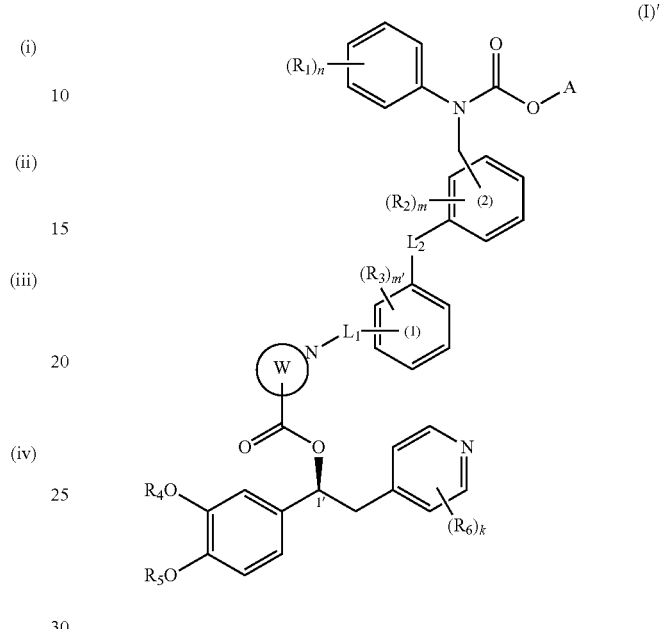

(I)'

The absolute configuration for carbon 1' is assigned on the basis of Cahn-Ingold-Prelog nomenclature based on groups'priorities.

In one preferred embodiment, for compounds of formula (I), absolute configuration at carbon (1) is (S).

In one embodiment, when A is a group of formula (i) as above defined, compounds of formula (I) may exist as at least four diastereoisomeric couples (Ia), (Ib), (Ic) and (Id) herebelow reported, which are comprised within the scope of the present invention. Moreover each couple of diastereoisomers (Ia), (Ib), (Ic), (Id) is constituted by a mixture of corresponding epimers at stereogenic center 2'.

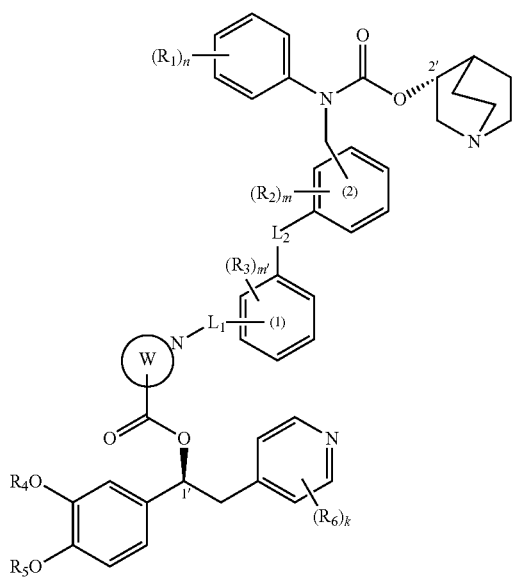

(Ia)

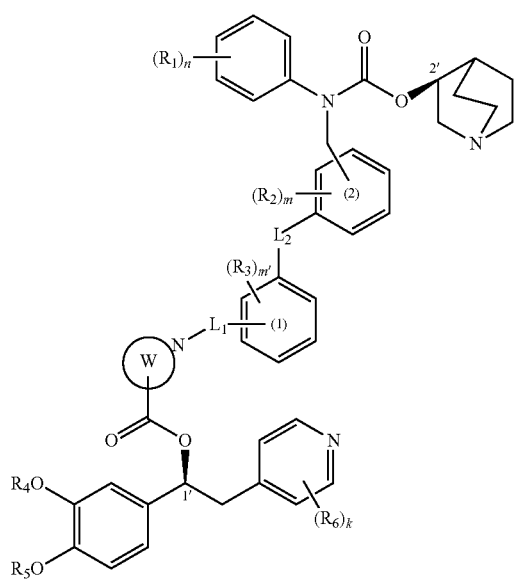
(Ib)

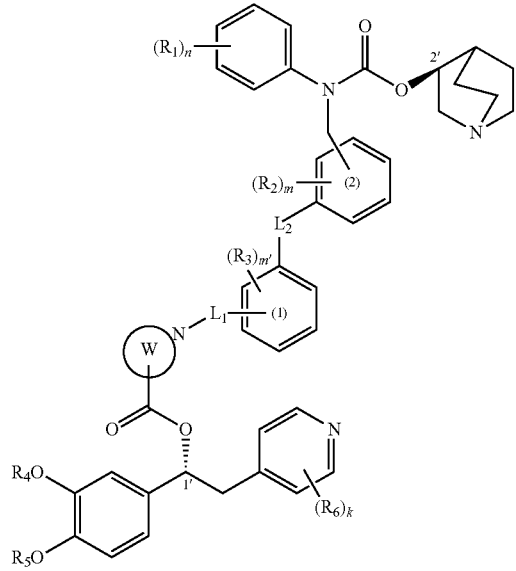
(Ic)

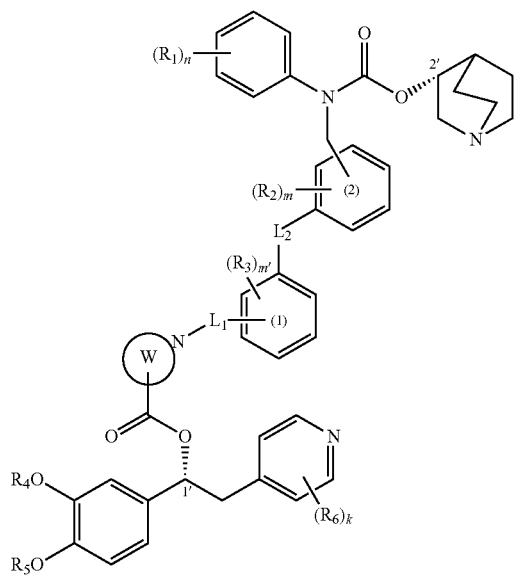
(Id)

It will be apparent to the skilled person that compounds of formula (Ia), (Ib), (Ic), (Id) may be also obtained as single diastereoisomers wherein the configuration at the stereogenic centre at carbon atom 2' is defined as (R) or (S).

In one embodiment, compounds of formula (Ia) are provided as above reported, or single diastereoisomers thereof.

It is to be understood that all preferred groups or embodiments described herebelow and hereabove for compounds of formula (I) may be combined among each other and apply to compounds of formula (IA), (IB), (IC), (Ia), (Ib), (Ic), (Id) and (I)' as well mutatis mutandis.

In one embodiment, the present invention provides compounds of formula (IA), which are N-oxides on the pyridine ring of compounds of formula (I), deuterated derivatives and pharmaceutically acceptable salts and solvates thereof:

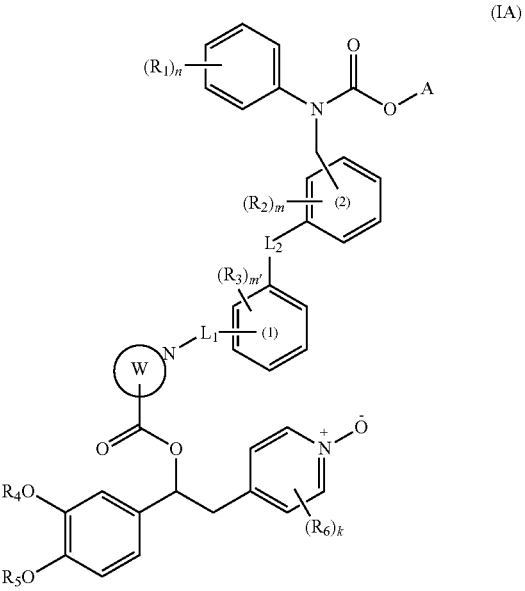
(IA)

wherein $R_1$, $R_2$, $R_3$, $R_4$, $R_5$, $R_6$, W, $L_1$, $L_2$, A, m, m', n and k are as described above.

In a preferred embodiment, k is 2 and $R_6$ are halogen atoms. In a further preferred embodiment such $R_6$ are two chlorine atoms at positions 3 and 5 of the pyridine ring.

In one preferred embodiment $R_5$ is selected from a ($C_1$-$C_6$) alkyl and ($C_1$-$C_6$) haloalkyl and $R_4$ is selected from ($C_3$-$C_7$) cycloalkyl or ($C_1$-$C_6$) alkyl which is optionally substituted by ($C_3$-$C_7$) cycloalkyl.

In another preferred embodiment, $R_4$ and $R_5$ are both methyl or $R_4$ is cyclopropylmethyl and $R_5$ is difluoromethyl.

A preferred compound of formula (I) is that wherein the group

is a saturated monocyclic heterocycloalkylene with 5 ring atoms, wherein one heteroatom is a nitrogen atom, linked to the group $L_1$ and represented by formula (IB):

(IB)

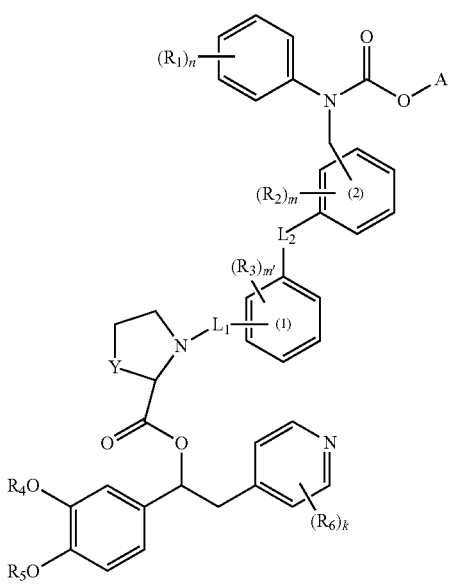

wherein
Y is selected from —(CH2)-, —S— and —N(H)—
L₁ is selected from —CO— and —SO₂—
and $R_1$, $R_2$, $R_3$, $R_4$, $R_5$, $R_6$, A, $L_2$, m, m', n and k are as defined above for compounds of formula (I); and the corresponding N-oxide on the pyridine ring, deuterated derivatives and pharmaceutically acceptable salts and solvates thereof.

Another preferred compound of formula (I) is that wherein the group

is a saturated monocyclic heterocycloalkylene with 4 ring atoms represented by formula (IC):

(IC)

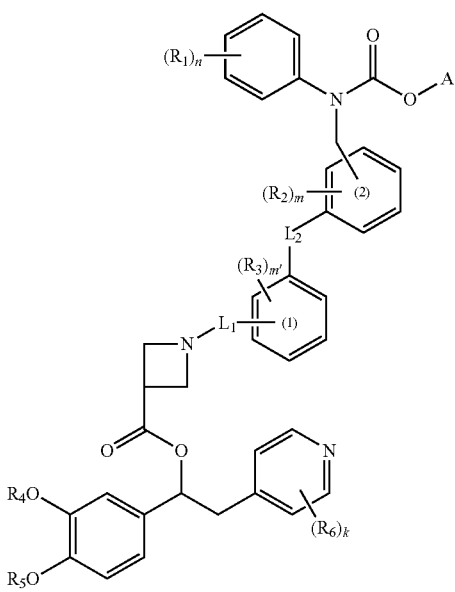

wherein
L₁ is selected from —CO— and —SO₂— and
$R_1$, $R_2$, $R_3$, $R_4$, $R_5$, $R_6$, A, $L_2$, m, m', n and k are as defined above for compounds of formula (I); and the corresponding N-oxide on the pyridine ring, deuterated derivatives and pharmaceutically acceptable salts and solvates thereof.

According to a preferred embodiment, the present invention provides the compounds reported below:

[(1S)-1-[3-(cyclopropylmethoxy)-4-(difluoromethoxy)phenyl]-2-(3,5-dichloro-1-oxido-pyridin-1-ium-4-yl)ethyl] (2S)-3-[3-[2-[[3-[(N-[(3R)-quinuclidin-3-yl]oxycarbonylanilino)methyl]benzoyl]amino]ethylcarbamoyl]phenyl]sulfonylthiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl] (2S)-3-[3-[[3-[(2-fluoro-N-[(3R)-quinuclidin-3-yl]oxycarbonyl-anilino)methyl]benzoyl]oxymethyl]phenyl]sulfonylthiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl] (2S)-3-[4-[[4-[(N-[(3R)-quinuclidin-3-yl]oxycarbonylanilino)methyl]phenoxy]methyl]benzoyl]thiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl] (2S)-3-[4-[[3-[(N-[(3R)-quinuclidin-3-yl]oxycarbonylanilino)methyl]phenoxy]methyl]benzoyl]thiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl]1-[4-[[4-[(N-[(3R)-quinuclidin-3-yl]oxycarbonylanilino)methyl]phenoxy]methyl]benzoyl]azetidine-3-carboxylate;

[(1S)-1-[3-(cyclopropylmethoxy)-4-(difluoromethoxy)phenyl]-2-(3,5-dichloro-1-oxido-pyridin-1-ium-4-yl)ethyl]1-[4-[[3-[(N-[(3R)-quinuclidin-3-yl]oxycarbonylanilino)methyl]phenoxy]methyl]benzoyl]azetidine-3-carboxylate;

and deuterated derivatives and pharmaceutically acceptable salts and solvates thereof.

The present invention also provides processes for the preparation of compounds of the invention.

Processes of preparation described below and reported in the following Schemes or reported in the synthetic procedures of Example 5 and Example 6 should not be viewed as limiting the scope of the synthetic methods available for the preparation of the compounds of the invention.

N-oxides of compounds of formula (I), represented by the formula (IA) wherein L₁=CO and L₂=CH₂O, can be obtained according to general synthetic routes reported in the following Scheme A or Scheme B, or following slightly modified procedures that the skilled person can easily apply. Some intermediates described in the following Schemes may also be commercially available.

In the following Schemes A and B, for compounds of formula IA to XVI, unless otherwise indicated, $R_1$, $R_2$, $R_3$, $R_4$, $R_5$, $R_6$, $L_1$, $L_2$, W, A, n, m, m' and k are as above defined.

In the following Schemes A and B compounds of formula (IA) are prepared starting from the pyridine N-oxides of formula (II) described in the co-pending International Patent Application No. PCT/EP2013/075526 (published as WO 2014/086852), which is incorporated herein by reference in its entirety. Any corresponding compound of formula (I) may be similarly obtained starting from the non-oxidized pyridines, analogues of compounds (II), described in the co-pending International Patent Application No. PCT/EP2013/075526 (published as WO 2014/086852), which is incorporated herein by reference in its entirety.

Scheme A
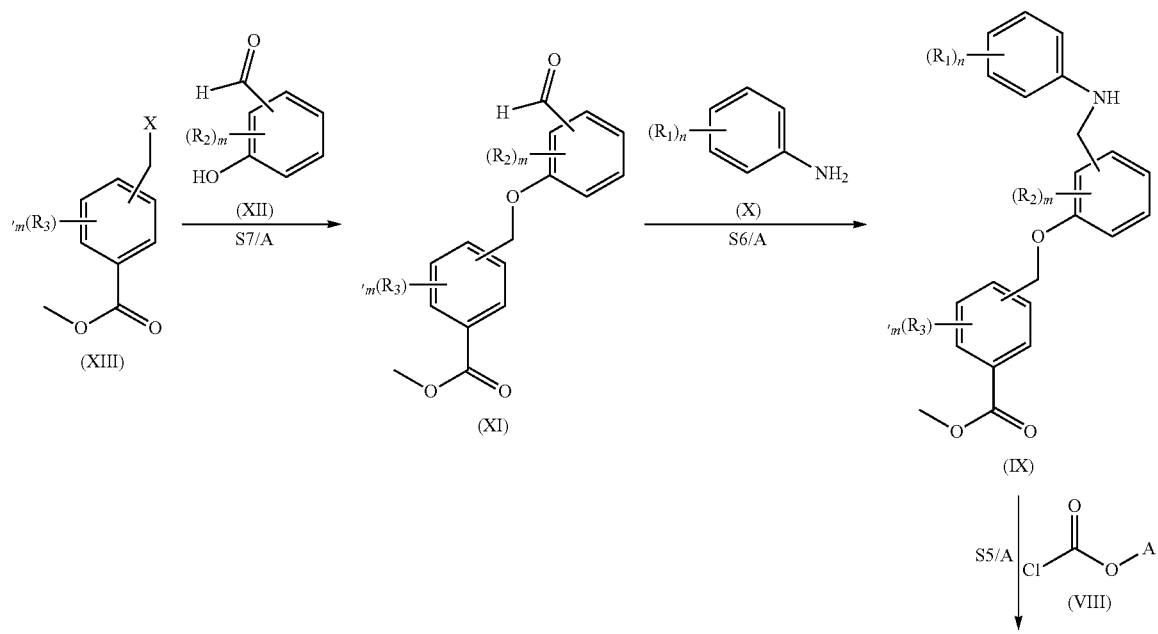
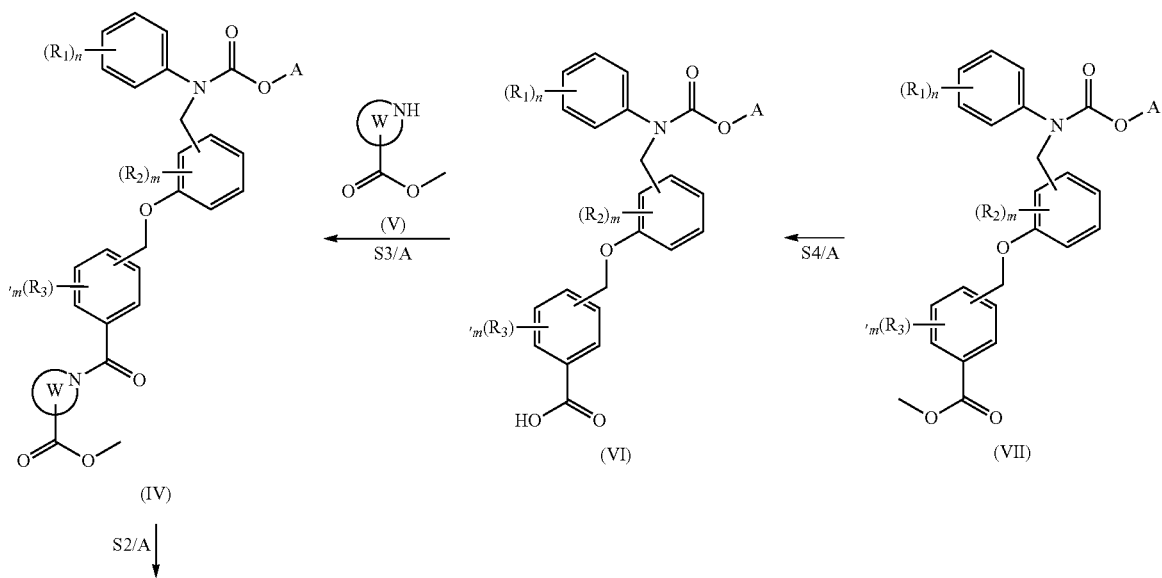

-continued
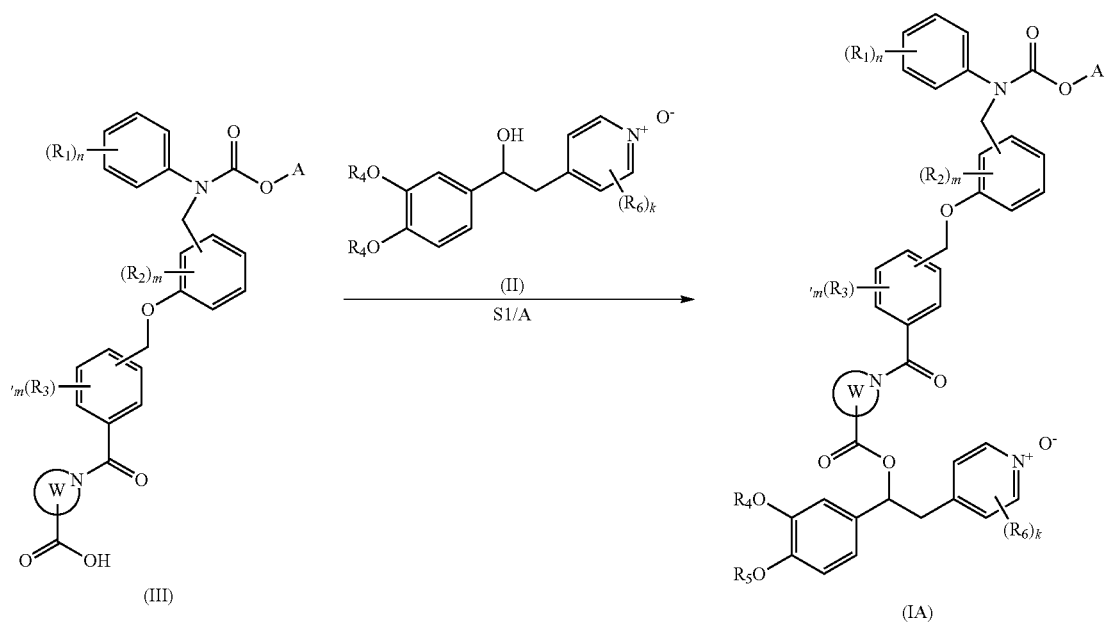
Scheme 1/A (S1/A)
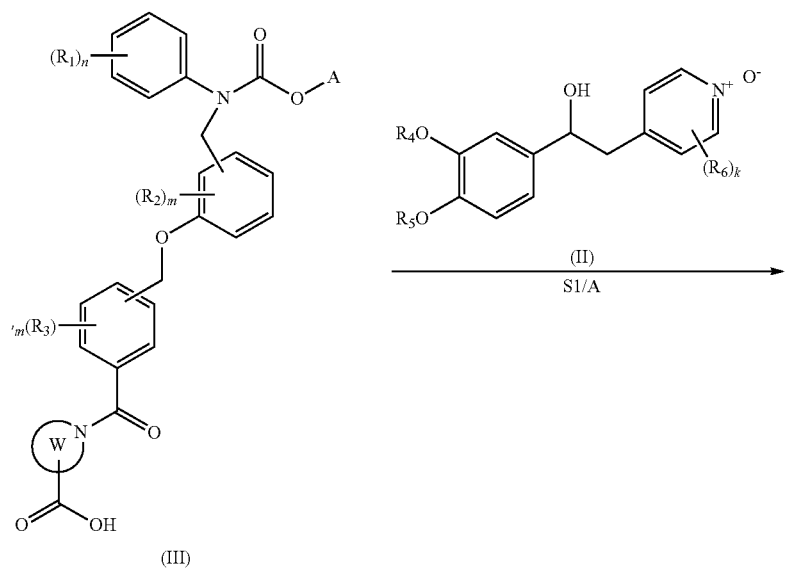

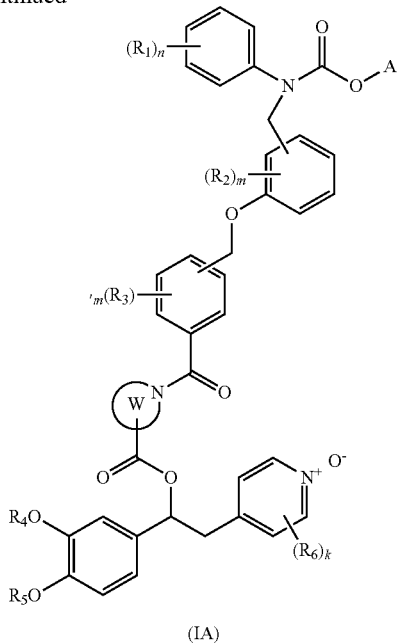

(IA)

Typical reaction conditions comprise reacting a compound of formula (III) with a compound of formula (II) in a suitable solvent, such as DCM or DMF in the presence of a coupling agent, such as EDC/DMAP or HATU, at an appropriate temperature, such as room (or ambient) temperature.

Compounds of formula (II) may be prepared as described in the co-pending International Patent Application No. PCT/EP2013/075526 (published as WO 2014/086852), which is incorporated herein by reference in its entirety.

Compounds of formula (III) may be prepared according to Scheme 2/A (S2/A) below by reaction of a compound of formula (IV) as below reported.

Scheme 2/A (S2/A)

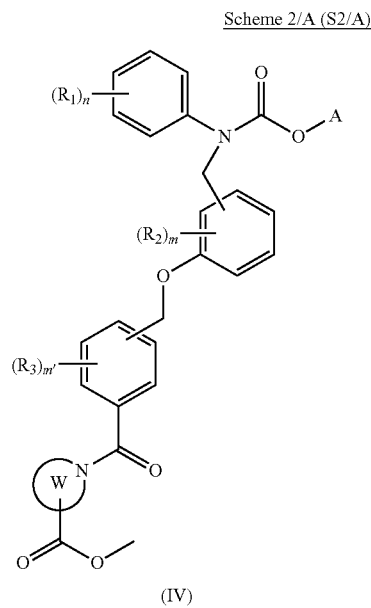

(IV)

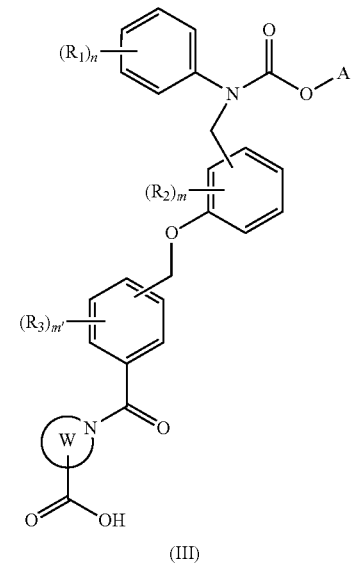

(III)

Typical reaction conditions comprise hydrolysis of a compound of formula (IV) in a suitable solvent mixture, such as THF/MeOH/water, in the presence of a suitable base, such as lithium hydroxide, at an appropriate temperature such as room temperature or 40° C.

Compounds of formula (IV) may be prepared according to Scheme 3/A (S3/A) below by reaction of a compound of formula (VI) with a compound of formula (V) as below reported.

Scheme 3/A (S3/A)

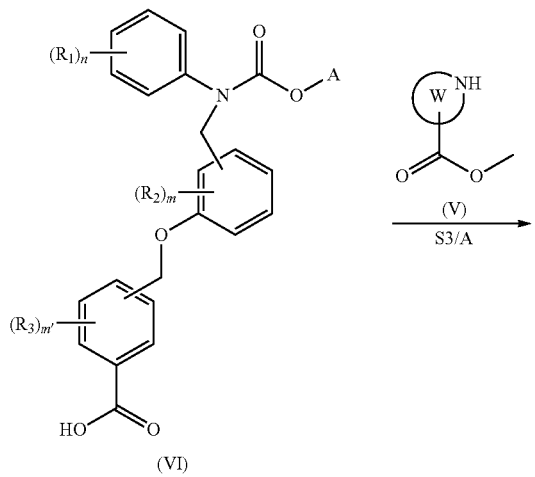

Scheme 4/A (S4/A)

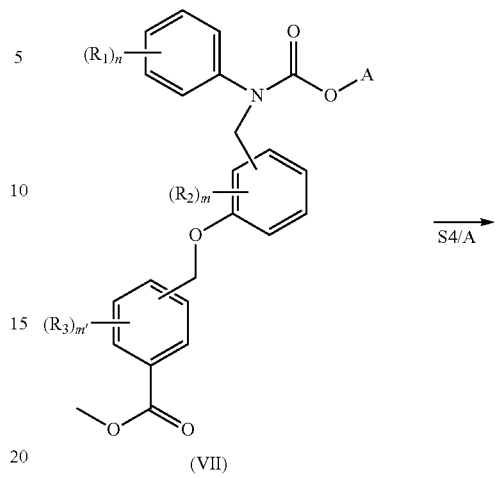

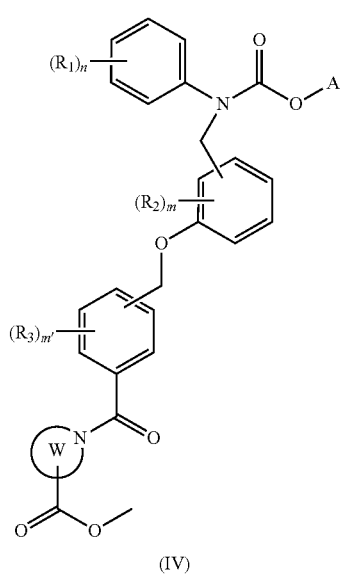

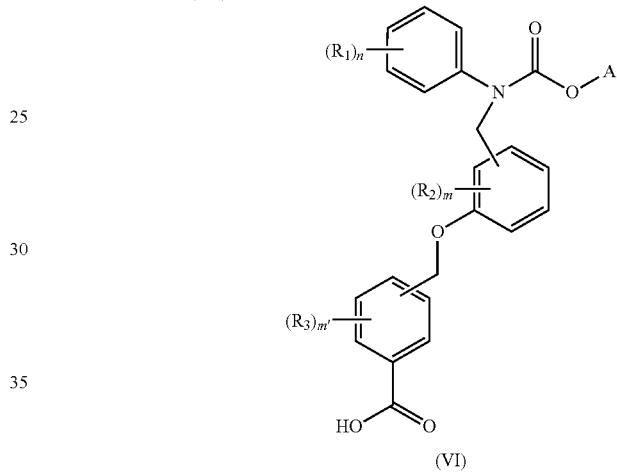

Typical reaction conditions comprise hydrolysis of a compound of formula (VII) in a suitable solvent mixture, such as THF/MeOH/water, in the presence of a suitable base, such as lithium hydroxide, at an appropriate temperature such as room temperature or 40° C.

Compounds of formula (VII) may be prepared according to Scheme 5/A (S5/A) below by reaction of a compound of formula (IX) with a compound of formula (VIII) as below reported.

Scheme 5/A (S5/A)

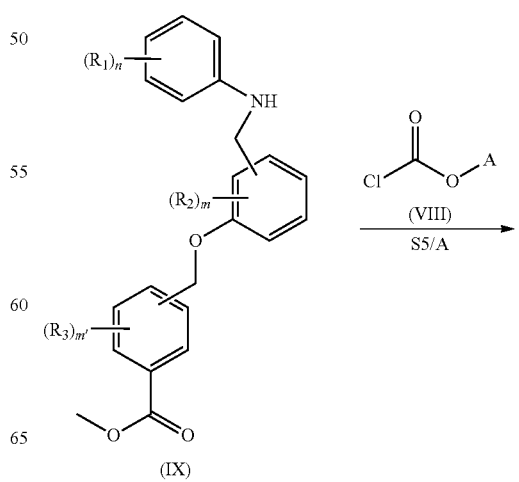

Typical reaction conditions comprise reacting a compound of formula (VI) with a compound of formula (V) in a suitable solvent, such as DCM or DMF in the presence of a coupling agent, such as EDC/DMAP or HATU, at an appropriate temperature, such as room (or ambient) temperature.

Compounds of formula (VI) may be prepared according to Scheme 4/A (S4/A) below by reaction of a compound of formula (VII) as below reported

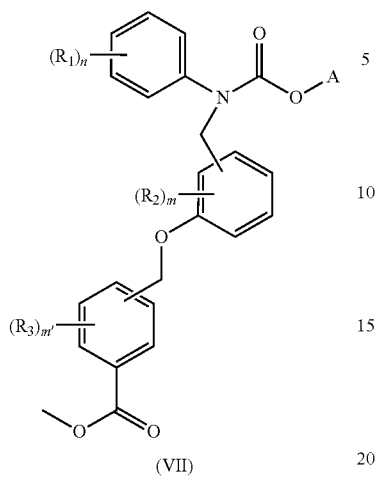

(VII)

Typical reaction conditions comprise reacting a compound of formula (IX) with a compound of formula (VIII) in a suitable solvent, such as CH$_3$CN or pyridine, and an optional catalyst, such as DMAP, at an appropriate temperature such as room (or ambient) temperature or 0° C. to 100° C.

Compounds of formula (II) may be prepared as described in the co-pending International Patent Application No. PCT/EP2013/075529 (published as WO 2014/086855), which is incorporated herein by reference in its entirety.

Compounds of formula (IX) may be prepared according to Scheme 6/A (S6/A) by reaction of a compound of formula (XI) with an appropriate compound of formula (X) as below reported.

Scheme 6/A (S6/A)

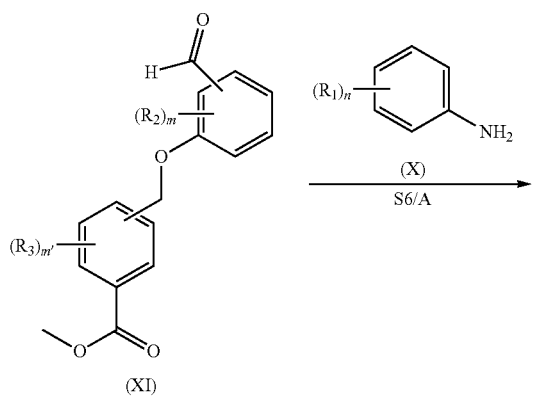

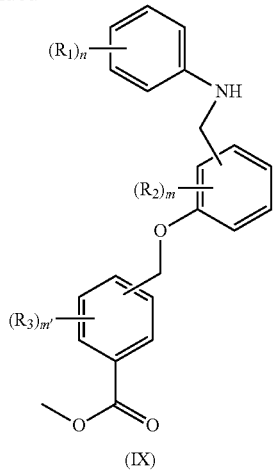

(IX)

Typical reaction conditions comprise reacting a compound of formula (XI) with a compound of formula (X) in a suitable solvent, such as ethanol, DCM or THF, in the presence of an acid, such as acetic acid, under reducing conditions, for example with sodium borohydride, sodium triacetoxyborohydride, sodium cyanoborohydride or by catalytic hydrogenation, and an optional catalyst, such as DMAP, at an appropriate temperature such as room (or ambient) temperature or 0° C. or 40° C. or 50° C.

Compounds of formula (XI) may be prepared according to Scheme 7/A (S7/A) by reaction of a compound of formula (XIII) with an appropriate compound of formula (XII) as below reported.

Scheme 7/A (S7/A)

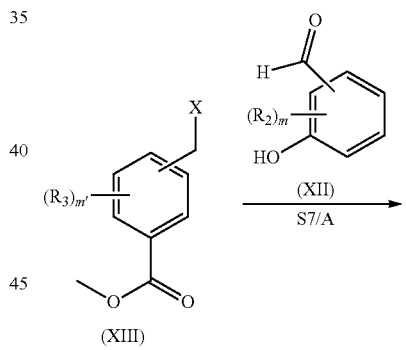

(XI)

Typical reaction conditions comprise reacting of a compound of formula (XIII) with a compound of formula (XII) in a suitable solvent, such as acetone, in the presence of a suitable base, such as potassium carbonate, at an appropriate temperature such as room (or ambient) temperature or 40° C.

Scheme B
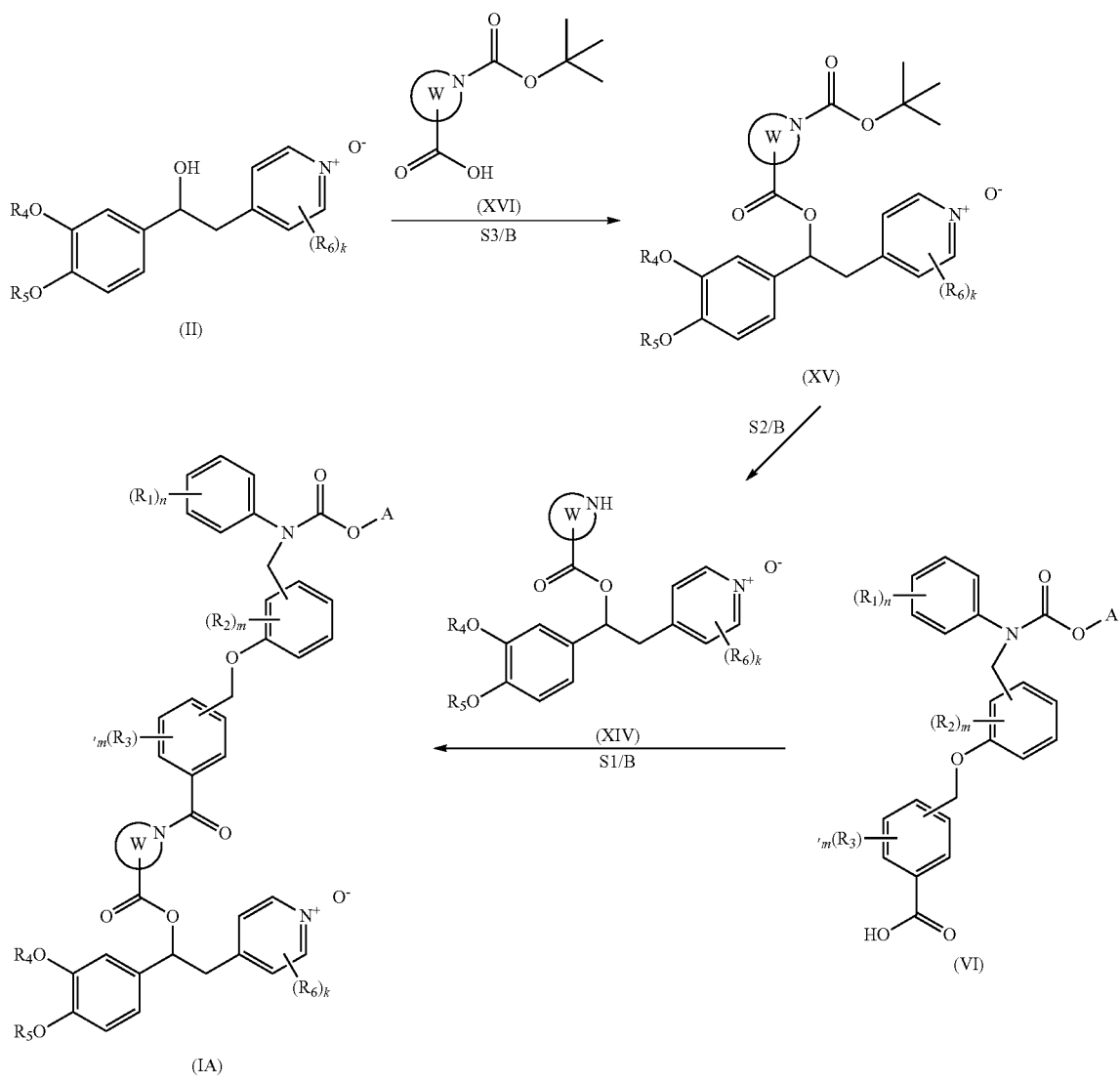
Scheme 1/B (S1/B)
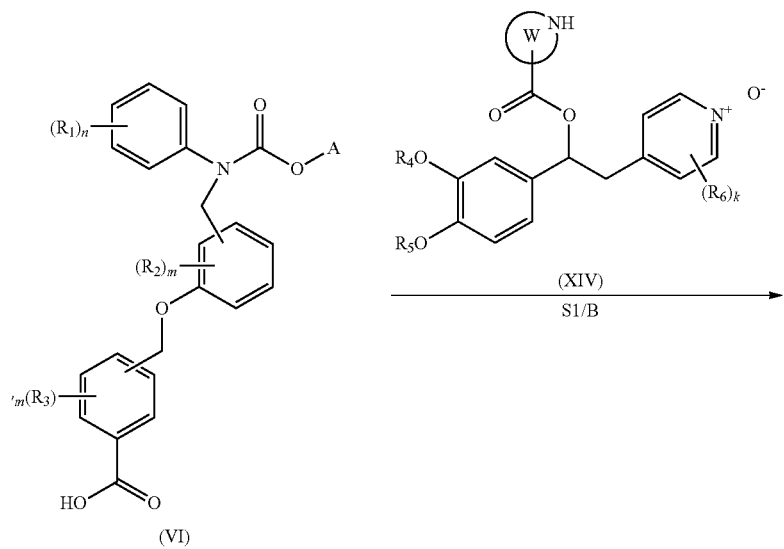

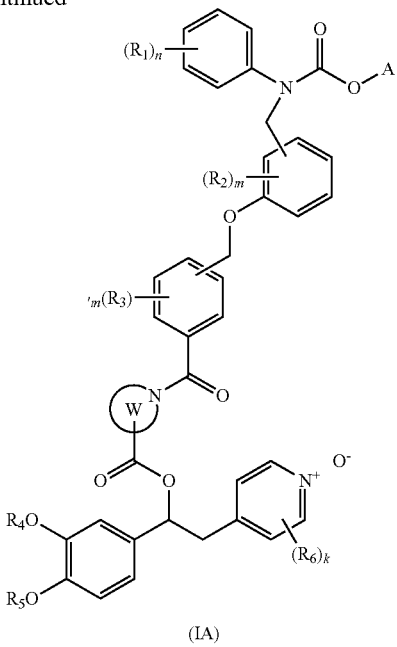

(IA)

Typical reaction conditions comprise reacting a compound of formula (VI) with a compound of formula (XIV) in a suitable solvent, such as DCM or DMF in the presence of a coupling agent, such as EDC/DMAP or HATU, at an appropriate temperature, such as room (or ambient) temperature.

Compounds of formula (VI) may be prepared as described in Scheme A above.

Compounds of formula (XIV) may be prepared as shown in Scheme 2/B (S2/B) below.

Scheme 2/B (S2/B)

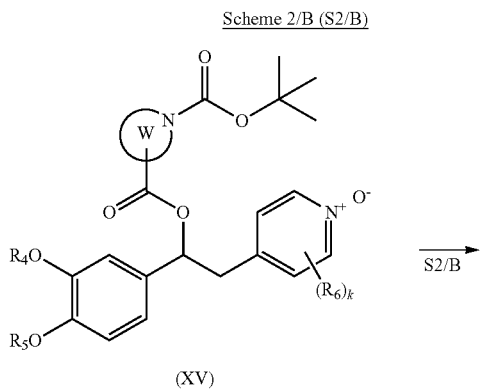

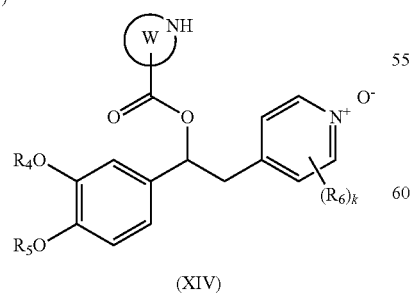

Typical reaction conditions comprise reacting a compound of formula (XV) with an acid such as HCl or TFA in a suitable solvent, such as dioxane, EtOAc or DCM at an appropriate temperature, such as room (or ambient) temperature or 0° C.

Compounds of formula (XV) may be prepared according to Scheme 3/B (S3/B) by reaction of a compound of formula (II) with a compound of formula (XVI) as below reported.

Scheme 3/B (S3/B)

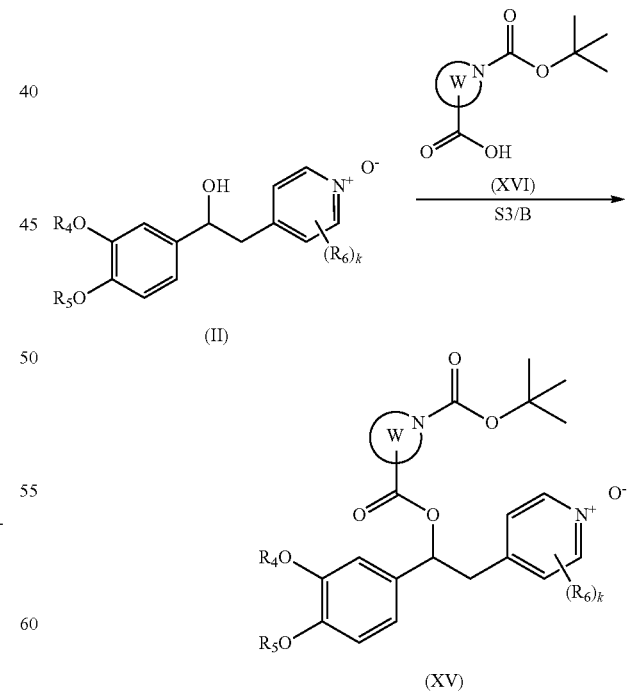

Typical reaction conditions comprise reacting a compound of formula (II) with a compound of formula (XVI) in a suitable solvent, such as DCM or DMF in the presence of a coupling agent, such as EDC/DMAP or HATU, at an appropriate temperature, such as room (or ambient) temperature.

The processes described are particularly advantageous as they are susceptible of being properly modulated, through any proper variant known to the skilled person, so as to obtain any of the desired compounds of the invention. Such variants are comprised within the scope of the present invention.

From all of the above, it should be clear to the skilled person that any of the described groups may be present as such or in any properly protected form.

In particular, functional groups present in the compounds of formula II to XXVI which could generate unwanted side reactions and by-products, need to be properly protected before the alkylation, acylation, coupling, oxidation or sulfonylation takes place. Likewise, subsequent deprotection of those same protected groups may follow upon completion of the said reactions.

According to the present invention, unless otherwise indicated, the term "protecting group" designates a protective group adapted to preserve the function of the group it is bound to. Typically, protective groups are used to preserve amino, hydroxy, or carboxyl functions. Appropriate protecting groups may thus include, for example, benzyl, benzyloxycarbonyl, t-butoxycarbonyl, alkyl or benzyl esters or the like, which are well known to those skilled in the art [see, for a general reference, T. W. Green; Protective Groups in Organic Synthesis (Wiley, N.Y. 1999), which is incorporated herein by reference in its entirety].

Likewise, selective protection and deprotection of any of the said groups, for instance including carbonyl, hydroxy or amino groups, may be accomplished according to very well-known methods commonly employed in organic synthetic chemistry.

The N-oxides on the 4-pyridinyl ring of the compounds of general formula (I) and embodiments thereof may be prepared according to methods available in the literature and well known to the skilled person. For instance they may be prepared by dissolving the compound of general formula (I) or embodiments thereof in $CH_2Cl_2$ or $CHCl_3$, then adding an oxidizing agent such as m-chloro perbenzoic acid (mCPBA) to the resulting solution. Other oxidizing agents which may be used are hydrogen peroxide, perbenzoic acid and peracetic acid.

Alternatively, in particular for those compounds comprising functional groups sensitive to oxidation, the corresponding N-oxides are prepared by carrying out the oxidation step before further functional groups are introduced.

In a preferred embodiment, the process for preparation of compounds of formula (I) or embodiments thereof is performed starting from N-oxide on the pyridine ring of compound of formula (VIII), thus allowing the preparation of compound of formula (I) or embodiments thereof in the form of N-oxides on the pyridine ring.

Optional salification of the compounds of formula (I) or N-oxides on the pyridine ring thereof may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

From all of the above, it should be clear to the skilled person that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

The present invention also provides pharmaceutical compositions of compounds of the invention in admixture with one or more pharmaceutically acceptable carriers, for example those described in Remington's Pharmaceutical Sciences Handbook, XVII Ed., Mack Pub., N.Y., U.S.A., which is incorporated herein by reference in its entirety.

Administration of the compounds of the invention or may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration. Various solid oral dosage forms may be used for administering the compounds of the invention including such solid forms as tablets, gelcaps, capsules, caplets, granules, lozenges and bulk powders. The compounds of the invention may be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms may also be used for administering the compounds of the invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the invention may be injected, for example, intravenously, in the form of an isotonic sterile solution. Other preparations are also possible.

Suppositories for rectal administration of the compounds of the present invention may be prepared by mixing the compound with a suitable excipient such as cocoa butter, salicylates and polyethylene glycols.

Formulations for vaginal administration may be in the form of cream, gel, paste, foam, or spray formula containing, in addition to the active ingredient, such suitable carriers as are known in the art.

For topical administration the pharmaceutical composition may be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metered aerosols or propellant-free inhalable formulations and may be administered through a suitable inhalation device which may be respectively selected from a dry powder inhaler, a pressurized metered dosed inhaler, or a nebulizer.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in the form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention may be administered as the sole active agent or in combination with other pharmaceutical active ingredients including those currently used in the treatment of respiratory disorders, e.g. beta2-agonists, antimuscarinic agents, corticosteroids, mitogen-activated protein kinases (P38 MAP kinase) inhibitors, nuclear factor kappa-B kinase subunit beta (IKK2) inhibitors, human neutrophil elastase (HNE) inhibitors, phosphodiesterase 4 (PDE4) inhibitors, leukotriene modulators, non-steroidal anti-inflammatory agents (NSAIDs) and mucus regulators.

The present invention also provides combinations of a compound of the invention, with β2-agonist selected from the group consisting of carmoterol, vilanterol (GSK-642444), indacaterol, milveterol, arformoterol, formoterol, salbutamol, levalbuterol, terbutaline, AZD-3199, olodaterol (BI-1744-CL), abediterol (LAS-100977), bambuterol, isoproterenol, procaterol, clenbuterol, reproterol, fenoterol and ASF-1020 and salts thereof.

The present invention also provides combinations of a compound of the invention, with a corticosteroid selected from the group consisting of fluticasone propionate, fluticasone furoate, mometasone furoate, beclometasone dipropionate, ciclesonide, budesonide, GSK 685698, and GSK 870086.

The present invention also provides combinations of a compound of the invention, with an antimuscarinic agent selected from the group consisting of aclidinium, tiotropium, ipratropium, trospium, glycopyrronium and oxitropium salts.

The present invention also provides combinations of a compound of the invention, with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TPI-PD3, ELB-353, CC-11050, GSK-256066, oglemilast, OX-914, tetomilast, MEM-1414 and RPL-554.

The present invention also provides combinations of a compound of the invention, with a P38 MAP kinase inhibitor selected from the group consisting of semapimod, talmapimod, pirfenidone, PH-797804, GSK-725, minokine and losmapimod and salts thereof.

In a preferred embodiment, the present invention provides combinations of a compound of the invention with an IKK2 inhibitor.

The present invention also provides combinations of a compound of the invention with a FINE inhibitor selected from the group consisting of AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C and prolastin inhaled.

The present invention also provides combinations of a compound of the invention with a leukotriene modulator selected from the group consisting of montelukast, zafirlukast and pranlukast.

The present invention also provides combinations of a compound of the invention with a NSAID selected from the group consisting of ibuprofen and ketoprofen.

The present invention also provides combinations of a compound of the invention with a mucus regulator selected from the group consisting of INS-37217, diquafosol, sibenadet, CS-003, talnetant, DNK-333, MSI-1956 and gefitinib.

The dosages of the compounds of the invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of the invention may be administered for example, at a dosage comprised between 0.001 and 1000 mg/day, preferably between 0.1 and 500 mg/day.

When they are administered by inhalation route, the dosage of the compounds of the invention is advantageously comprised between 0.01 and 20 mg/day, preferably between 0.1 and 10 mg/day.

Preferably, the compounds of the invention alone or combined with other active ingredients may be administered for the prevention and/or treatment of any obstructive respiratory disease such as asthma, chronic bronchitis, and chronic obstructive pulmonary disease (COPD).

The compounds of the invention may be administered for the prevention and/or treatment of any disease wherein PDE4 inhibition or M3 antagonism is required. Said disease include: allergic disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, artherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, pruritus in the anogenital area, alopecia areata, hypertrophic scars, discoid lupus erythematosus, systemic lupus erythematosus, follicular and wide-area pyodermias, endogenous and exogenous acne, acne rosacea, Behçet's disease, anaphylactoid purpura nephritis, inflammatory bowel disease, leukemia, multiple sclerosis, gastrointestinal diseases, autoimmune diseases and the like.

They also include neurological and psychiatric disorders such as Alzheimer's disease, multiple sclerosis, amylolaterosclerosis (ALS), multiple systems atrophy (MSA), schizophrenia, Parkinson's disease, Huntington's disease, Pick's disease, depression, stroke, and spinal cord injury.

Other features of the invention will become apparent in the course of the following descriptions of exemplary embodiments which are given for illustration of the invention and are not intended to be limiting thereof.

EXAMPLES

Abbreviations

DCC=N,N'-dicyclohexylcarbodiimide;
HOBt=hydroxybenzotriazole;
HATU=(dimethylamino)-N,N-dimethyl(3H-[1,2,3]triazolo [4,5-b]pyridin-3-yloxy)methaniminium hexafluorophosphate;
EDC=1-ethyl-3-(3-dimethylaminopropyl) carbodiimide hydrochloride;

DMAP=4-dimethylaminopyridine;
DMF=dimethylformamide;
DMSO=dimethyl sulfoxide;
EtOAc=ethyl acetate;
RT=room temperature;
THF=tetrahydrofuran;
DCM=dichloromethane;
MeOH=methyl alcohol;
EtOH=ethyl alcohol;
LHMDS=lithium bis(trimethylsilyl)amide;
m-CPBA=meta-Chloroperoxybenzoic acid;
TFA=trifluoroacetic acid;
LC-MS=liquid chromatography/mass spectrometry;
NMR=nuclear magnetic resonance;
HPLC=high pressure liquid chromatography;
MPLC=medium pressure liquid chromatography;
SFC=supercritical fluid chromatography General Experimental Details Analytical Methods
Liquid Chromatography-Mass Spectrometry
Method 1
LC-MS was performed on a Waters 2795 Alliance HT HPLC with Waters 2996 Diode Array Detector coupled to a Micromass ZQ, single quadrupole mass spectrometer using a Phenomenex Luna C18 (2) column (5 µm, 100×4.6 mm plus guard cartridge) with a linear gradient of 5-95% acetonitrile/water (with 0.1% formic acid in each mobile phase) within 3.5 minutes and held at 95% for 2.0 minutes.
Method 2
LC-MS was performed on a Waters 2795 Alliance HT HPLC with Waters 2996 Diode Array Detector coupled to a Micromass ZQ, single quadrupole mass spectrometer using a Waters Xterra MS C18 column (5 µm, 100×4.6 mm plus guard cartridge) being initially held at 5% acetonitrile/water (with 10 mM ammonium bicarbonate in the aqueous mobile phase) for 0.5 minutes, followed by a linear gradient of 5-95% within 3.5 minutes and then held at 95% for 1.5 minutes.
NMR
$^1$H Nuclear magnetic resonance (NMR) spectroscopy was carried out using a Bruker instrument operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; m, multiplet; br, broad.
Preparative Reverse-Phase HPLC Conditions
Preparative HPLC purification was performed by reverse phase HPLC using a Waters Fractionlynx preparative HPLC system (2525 pump, 2996/2998 UV/VIS detector, 2767 liquid handler) or an equivalent HPLC system such as a Gilson Trilution UV directed system. The Waters 2767 liquid handler acted as both auto-sampler and fraction collector.
The columns used for the preparative purification of the compounds were a Waters Sunfire OBD Phenomenex Luna Phenyl Hexyl or Waters Xbridge Phenyl at 10 µm 19×150 mm or Waters CSH Phenyl Hexyl, 19×150, 5 µm column.
Appropriate focused gradients were selected based on acetonitrile and methanol solvent systems under either acidic or basic conditions.
The modifiers used under acidic/basic conditions were formic acid or trifluoroacetic acid (0.1% V/V) and ammonium bicarbonate (10 mM) respectively.

The purification was controlled by Waters Fractionlynx software through monitoring at 210-400 nm, and triggered a threshold collection value at 260 nm and, when using the Fractionlynx, the presence of target molecular ion as observed under APi conditions. Collected fractions were analysed by LCMS (Waters Acquity systems with Waters SQD).
Compound Preparation
Where the preparation of starting materials is not described, these are commercially available, known in the literature, or readily obtainable by those skilled in the art using standard procedures. Where it is stated that compounds were prepared "analogously" or "similarly" to earlier examples or intermediates, it will be appreciated by the skilled person that the reaction time, number of equivalents of reagents and temperature can be modified for each specific reaction and that it may be necessary or desirable to employ different work-up or purification techniques.
Flash chromatography refers to silica gel chromatography and is carried out using an Isolera MPLC system (manufactured by Biotage); pre-packed silica gel cartridges (supplied by Biotage); or using conventional glass column chromatography.
In the procedures that follow, after each starting material, reference to a compound number may be provided. This is provided merely for assistance to the skilled chemist. The starting material may not necessarily have been prepared from the batch referred to.
Many of the compounds described in the following Examples have been prepared from stereochemically pure starting materials, for example 95% enantiomeric excess (ee).
The stereochemistry of the compounds in the Examples, where indicated, has been assigned on the assumption that absolute configuration at resolved stereogenic centers of staring materials is maintained throughout any subsequent reaction conditions.

Intermediate 1. Methyl 4-((3-formylphenoxy)methyl)benzoate

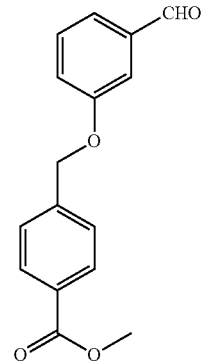 [SMILES: COC(=O)c1ccc(COc2cccc(C=O)c2)cc1]

A slurry of methyl 4-(bromomethyl)benzoate (1.4 g, 6.14 mmol), K$_2$CO$_3$ (1.02 g, 7.37 mmol), 3-hydroxybenzaldehyde (899 mg, 7.37 mmol) in acetone (20 mL) was stirred at room temperature for 16 hours. The solids were filtered, the filtrate partitioned between EtOAc (50 mL) and water (20 mL). The layers were separated and the aqueous phase back-extracted with EtOAc (3×30 mL) The combined organic phases were washed with brine (30 mL) and dried over MgSO$_4$. The solvent was removed in vacuo and the residue was purified via silica gel chromatography (eluting with 0-20% isohexane/EtOAc) to give the title compound (464 mg, 28% yield) as a white solid.

¹H NMR (400 MHz, CDCl₃): δ 9.96 (s, 1H), 8.06 (d, J=8.3 Hz, 2H), 7.50 (d, J=8.4 Hz, 2H), 7.48-7.44 (m, 3H), 7.27-7.23 (m, 1H), 5.18 (s, 2H), 3.92 (s, 3H).

LCMS (Method 2): [MH+]=270 at 3.48 min.

The following compound was synthesized in a similar way to Intermediate 1.

| Structure | Intermediate number | Analytical Data |
|---|---|---|
| 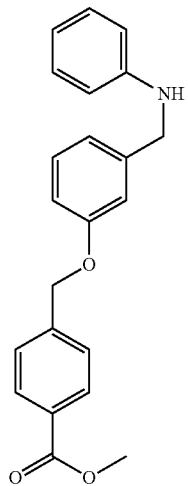 | Intermediate 2 | ¹H NMR (400 MHz, CDCl₃): δ 9.88 (s, 1 H), 8.07 (d, J = 8.1 Hz, 2 H), 7.85-7.82 (m, 2 H), 7.50 (d, J = 8.3 Hz, 2 H), 7.07 (d, J = 8.8 Hz, 2 H), 5.20 (s, 2 H), 3.92 (s, 3 H). LCMS (Method 1): [MH+] = 270 at 4.12 min. |

Intermediate 3. Methyl 4-[[3-(anilinomethyl)phenoxy]methyl]benzoate

To a stirred solution of methyl 4-((3-formylphenoxy)methyl)benzoate (464 mg, 1.72 mmol) in anhydrous DCM (8 mL) was added aniline (0.63 mL, 6.87 mmol) followed by glacial acetic acid (0.46 mL, 6.87 mmol). The reaction was stirred at room temperature for 18 hours. Sodium triacetoxyborohydride (1.52 g, 6.87 mmol) was added and the reaction was stirred at room temperature for 2 hours. The mixture was diluted with DCM (100 mL). The organic layer was washed with 1 N HCl (3×30 mL) and saturated aqueous NaHCO₃ (30 mL) and passed through a hydrophobic frit. The solvent was removed in vacuo to afford the title compound as an oil that solidifies on standing (380 mg, 64% yield).

¹H NMR (400 MHz, CDCl₃): δ 8.04 (d, J=8.3 Hz, 2H), 7.47 (d, J=8.1 Hz, 2H), 7.25 (t, J=8.0 Hz, 1H), 7.19-7.14 (m, 2H), 7.01-6.96 (m, 2H), 6.86 (dd, J=2.3, 8.1 Hz, 1H), 6.71 (dd, J=7.3, 7.3 Hz, 1H), 6.61 (d, J=7.8 Hz, 2H), 5.10 (s, 2H), 4.30 (s, 2H), 4.07 (s, 1H), 3.92 (s, 3H).

LCMS (Method 1): [MH+]=348 at 4.57 min.

The following compound was synthesized in a similar way to Intermediate 3.

| Structure | Intermediate number | Analytical Data |
|---|---|---|
| 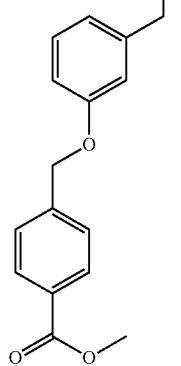 | Intermediate 4 | ¹H NMR (400 MHz, CDCl3): δ 8.05 (d, J = 8.3 Hz, 2 H), 7.50 (d, J = 8.3 Hz, 2 H), 7.30 (d, J = 8.0 Hz, 2 H), 7.19-7.14 (m, 2 H), 6.95-6.92 (m, 2 H), 6.72 (t, J = 7.6 Hz, 1 H), 6.63 (d, J = 7.6 Hz, 2 H), 5.12 (s, 2 H), 4.26 (s, 2 H), 3.92 (s, 3 H), NH not visible. |

Intermediate 5. Methyl 4-[[3-[(N-[(3R)-quinuclidin-3-yl]oxycarbonylanilino)methyl]-phenoxy]methyl]benzoate A suspension of methyl 4-[[3-(anilinomethyl)phenoxy]methyl]benzoate (380 mg, 1.1 mmol) and (R)-quinuclidin-3-yl carbonochloridate hydrochloride (described in the co-pending International Patent Application No. PCT/EP2013/075529 (published as WO 2014/086855) as Intermediate 16) (300 mg, 1.33 mmol) in anhydrous CH₃CN (5 mL) was heated to 100° C. for 15 min under microwave irradiation. After cooling to room temperature, the mixture was diluted with EtOAc (50 mL) and washed with saturated aqueous NaHCO₃ (20 mL) The layers were separated and the organic phase was dried over Na$_2$SO$_4$, filtered and the solvent was removed in vacuo to yield the title compound (419 mg, 76% yield) which was used directly in the next step without any further purification.

$^1$H NMR (400 MHz, CDCl$_3$): δ 8.04 (d, J=8.3 Hz, 2H), 7.47 (d, J=8.1 Hz, 2H), 7.32-7.25 (m, 3H), 7.24-7.16 (m, 2H), 7.12-7.04 (m, 2H), 6.85 (d, J=8.1 Hz, 2H), 5.08 (s, 2H), 4.84 (dd, J=13.7, 17.5 Hz, 2H), 4.81-4.75 (m, 1H), 3.92 (s, 3H), 3.19 (ddd, J=2.1, 8.2, 14.7 Hz, 1H), 2.75-2.55 (m, 5H), 1.98-1.91 (m, 1H), 1.66-1.57 (m, 1H), 1.56-1.46 (m, 1H), 1.45-1.34 (m, 1H), 1.28-1.16 (m, 1H). LCMS (Method 1): [MH+]= 501 at 2.94 min.

The following compound was synthesized in a similar way to Intermediate 5

A stirred solution of methyl 4-[[3-[(N-[(3R)-quinuclidin-3-yl]oxycarbonylanilino)methyl]phenoxy]methyl]benzoate (419 mg, 0.84 mmol) in THF (2 mL) and methanol (2 mL) was added with an aqueous solution of 1 N lithium hydroxide (1.7 mL, 1.68 mmol). The reaction was stirred at room temperature for 18 hours. The mixture was cooled to 0° C. and acidified by addition of 2N hydrochloric acid dropwise to pH≈2-3. The mixture was allowed to warm to room temperature and the solvent removed in vacuo and azeotroped with toluene to dryness. This crude material was dissolved in dimethylformamide (5 mL) and ⅔ of the solution was used in the next step. Methyl azetidine-3-carboxylate hydrochloride (104 mg, 0.69 mmol), 4-(dimethylamino)pyridine (38 mg,

| Structure | Intermediate number | Analytical Data |
|---|---|---|
| 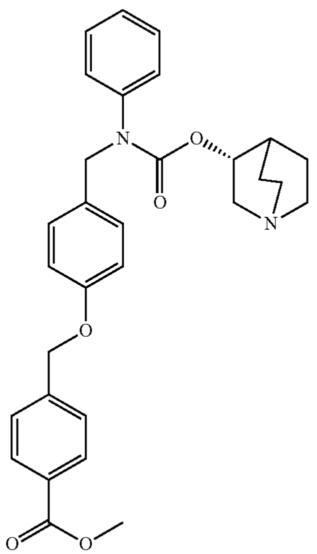 [SMILES: COC(=O)c1ccc(COc2ccc(CN(C(=O)O[C@H]3CN4CCC3CC4)c3ccccc3)cc2)cc1] | Intermediate 6 | $^1$H NMR (400 MHz, CDCl3): δ 8.04 (d, J = 8.3 Hz, 2 H), 7.48 (d, J = 8.3 Hz, 2 H), 7.29 (t, J = 7.2 Hz, 2 H), 7.20 (d, J = 7.4 Hz, 1 H), 7.17-7.13 (m, 2 H), 7.11-7.05 (m, 2 H), 6.88 (d, J = 8.6 Hz, 2 H), 5.09 (s, 2 H), 4.79 (s, 2 H), 4.78-4.75 (m, 1 H), 3.91 (s, 3 H), 3.20 (ddd, J = 7.4, 7.4, 7.4 Hz, 1 H), 2.79-2.55 (m, 5 H), 2.00-1.92 (m, 1 H), 1.68-1.57 (m, 1 H), 1.57-1.46 (m, 1 H), 1.46-1.36 (m, 1 H), 1.28-1.22 (m, 1 H). LCMS (Method 1): [MH+] = 501 at 2.91 min. |

Intermediate 7. Methyl 1-[4-[[3-[(N-[(3R)-quinuclidin-3-yl]oxycarbonylanilino)-methyl]phenoxy]methyl]benzoyl]azetidine-3-carboxylate

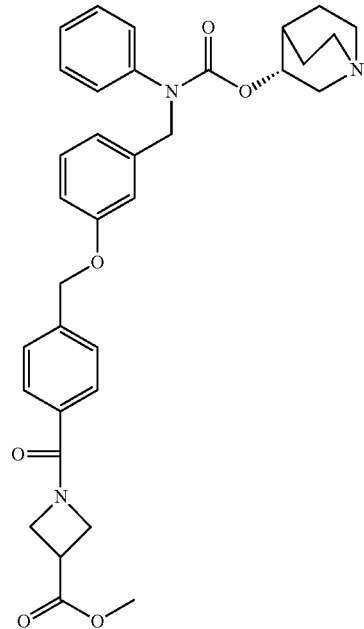 [SMILES: COC(=O)C1CN(C(=O)c2ccc(COc3cccc(CN(C(=O)O[C@H]4CN5CCC4CC5)c4ccccc4)c3)cc2)C1]

0.32 mmol) followed by N-(3-dimethylaminopropyl)-N'-ethylcarbodiimide hydrochloride (182 mg, 0.95 mmol) were then added and the reaction mixture was stirred at room temperature for 18 hours. The solvent was removed in vacuo and the residue was partitioned between EtOAc (50 mL) and water. The organic phase was dried over Na$_2$SO$_4$, filtered and the solvent was removed in vacuo to yield the title compound as an oil that solidifies on standing (190 mg, 52% yield over two steps).

$^1$H NMR (400 MHz, CDCl$_3$): δ 7.64 (d, J=8.1 Hz, 2H), 7.47-7.41 (m, 2H), 7.33-7.25 (m, 2H), 7.25-7.17 (m, 3H), 7.14-7.06 (m, 2H), 6.88-6.81 (m, 2H), 5.05 (s, 2H), 4.85 (dd, J=14.9, 18.6 Hz, 2H), 4.78 (dd, J=4.5, 7.7 Hz, 1H), 4.61-4.44 (m, 1H), 4.40 (t, J=9.3 Hz, 1H), 4.37-4.19 (m, 2H), 3.76 (s, 3H), 3.53-3.42 (m, 1H), 3.18 (ddd, J=2.1, 8.1, 14.7 Hz, 1H), 2.76-2.53 (m, 5H), 1.96-1.90 (m, 1H), 1.65-1.57 (m, 1H), 1.56-1.33 (m, 2H), 1.28-1.17 (m, 1H). LCMS (Method 2): [MH+]=584 at 3.64 min.

The following compound was synthesized in a similar way to Intermediate 7.

| Structure | Intermediate number | Analytical Data |
|---|---|---|
| 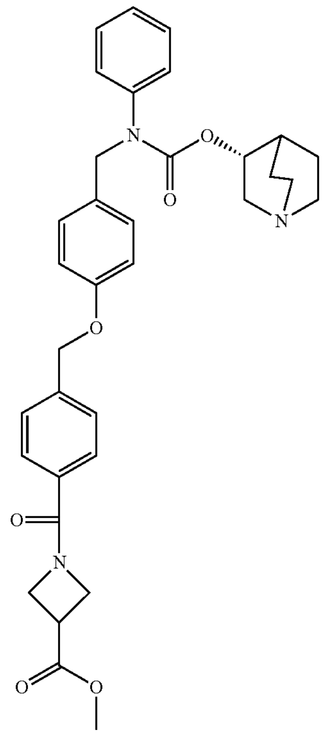 [SMILES: COC(=O)C1CN(C(=O)c2ccc(COc3ccc(CN(C(=O)O[C@H]4CN5CCC4CC5)c4ccccc4)cc3)cc2)C1] | Intermediate 8 | ¹H NMR (400 MHz, DMSO): δ 7.64 (d, J = 8.0 Hz, 2 H), 7.50 (d, J = 8.0 Hz, 2 H), 7.33 (t, J = 7.6 Hz, 2 H), 7.26 (d, J = 7.8 Hz, 2 H), 7.21 (t, J = 7.3 Hz, 1 H), 7.16 (d, J = 8.3 Hz, 2 H), 6.94 (d, J = 8.3 Hz, 2 H), 5.12 (s, 2 H), 4.97-4.90 (m, 1 H), 4.86 (d, J = 16.3 Hz, 1 H), 4.80 (d, J = 15.5 Hz, 1 H), 4.48 (t, J = 8.9 Hz, 1 H), 4.36 (t, J = 7.1 Hz, 1 H), 4.24 (t, J = 9.6 Hz, 1 H), 4.09 (dd, J = 9.9, 5.9 Hz, 1 H), 3.67 (s, 3 H), 3.66-3.61 (m, 1 H), 3.61-3.53 (m, 1 H), 3.25 (d, J = 13.9 Hz, 1 H), 3.17-3.09 (m, 3 H), 3.05-2.93 (m, 1 H), 2.14 (s, 1 H), 1.86-1.75 (m, 2 H), 1.65-1.44 (m, 2 H). LCMS (Method 1): [MH+] = 584 at 2.64 min. |

Intermediate 9. [(1S)-1-[3-(Cyclopropylmethoxy)-4-(difluoromethoxy)phenyl]-2-(3,5-dichloro-1-oxido-pyridin-1-ium-4-yl)ethyl](2S)-thiazolidine-2-carboxylate hydrochloride Step 1. Preparation of O3-tert-butyl O2-[(1S)-1-[3-(cyclopropylmethoxy)-4-(difluoromethoxy)phenyl]-2-(3,5-dichloro-1-oxido-pyridin-1-ium-4-yl)ethyl](2S)-thiazolidine-2,3-dicarboxylate

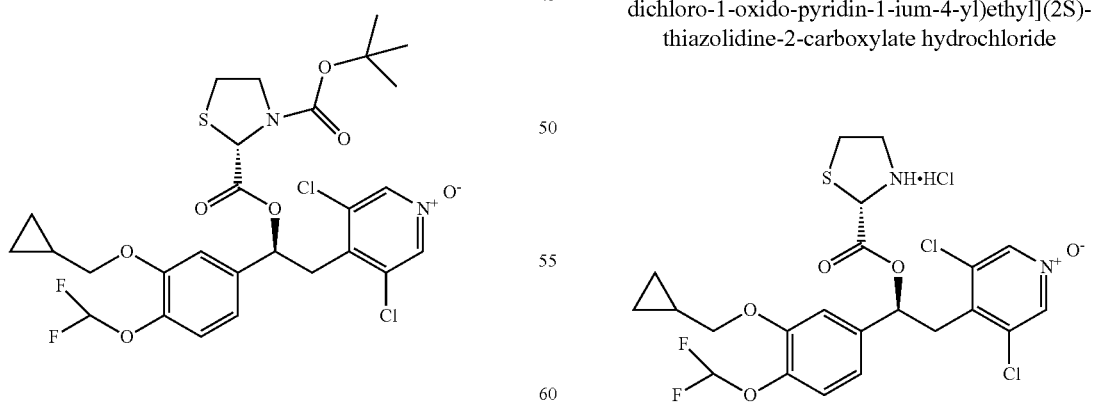

(1S)-1-[3-(Cyclopropylmethoxy)-4-(difluoromethoxy)phenyl]-2-(3,5-dichloro-1-oxido-pyridin-1-ium-4-yl)ethanol (843 mg, 2.01 mmol), (2S)-3-tert-butoxycarbonylthiazolidine-2-carboxylic acid (749 mg, 3.21 mmol), 4-(dimethylamino)pyridine (245 mg, 2.006 mmol) and N-(3-dimethylaminopropyl)-N'-ethylcarbodiimide hydrochloride (1.154 g, 6.02 mmol) were dissolved in DMF (10 ml). The reaction mixture was stirred at room temperature for 2 hours and then was diluted with water. The precipitate was washed with water, dissolved in EtOAc and extracted with 1 N HCl, saturated aqueous Na₂CO₃ and brine. The organic phase was dried over Na₂SO₄ and concentrated in vacuo to give the title compound as a thick oil (1.2 g, 94%). MS/ESI+ [MH+]= 635.2

Step 2. Preparation of [(1S)-1-[3-(cyclopropyl-methoxy)-4-(difluoromethoxy)phenyl]-2-(3,5-dichloro-1-oxido-pyridin-1-ium-4-yl)ethyl](2S)-thiazolidine-2-carboxylate hydrochloride O-3-tert-butyl O2-[(1S)-1-[3-(cyclopropylmethoxy)-4-(difluoromethoxy)phenyl]-2-(3,5-dichloro-1-oxido-pyridin-1-ium-4-yl)ethyl](2S)-thiazolidine-2,3-dicarboxylate (4.22 g, 6.64 mmol) was dissolved in EtOAc (10 mL). HCl solution in EtOAc (50 mL, 4.2 M, 210 mmol) was added and the reaction was stirred at room temperature for 5 min. The resulting white precipitate was filtered, washed with EtOAc and hexane, and dried in vacuo to yield the title compound as a pale yellow solid (3.19 g, 84%).

$^1$H NMR (400 MHz, DMSO) δ 8.57 (s, 2H), 7.19 (d, J=7.9 Hz, 1H), 7.12 (d, J=1.8 Hz, 1H), 7.08 (t, J=75 Hz, 1H), 6.93-7.00 (m, 1H), 5.89-5.98 (m, 1H), 5.12 (s, 1H), 3.91 (d, J=7.1 Hz, 2H), 3.37-3.47 (m, 1H), 3.10-3.31 (m, 3H), 2.77-2.93 (m, 2H), 1.05-1.36 (m, 1H), 0.51-0.63 (m, 2H), 0.34 (d, J=4.9 Hz, 2H). MS/ESI+[MH+]=535.2

Example 1

[(1S)-1-[3-(Cyclopropylmethoxy)-4-(difluoromethoxy)phenyl]-2-(3,5-dichloro-1-oxido-pyridin-1-ium-4-yl)ethyl]1-[4-[[3-[(N-[(3R)-quinuclidin-3-yl]oxycarbonylanilino)methyl]phenoxy]methyl]benzoyl]azetidine-3-carboxylate

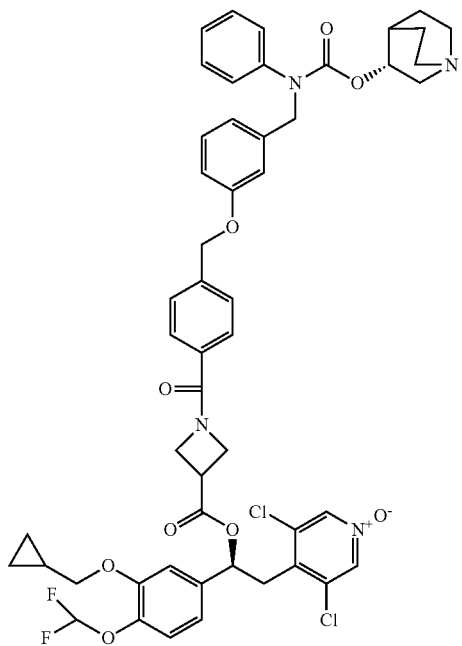

A solution of methyl 1-[4-[[3-[(N-[(3R)-quinuclidin-3-yl]oxycarbonylanilino)methyl]phenoxy]methyl]benzoyl]azetidine-3-carboxylate (Intermediate 7 above described) (190 mg, 0.32 mmol) in THF (3 mL) and methanol (3 mL) was added with an aqueous solution of 1N lithium hydroxide (0.64 mL, 0.64 mmol). The reaction was stirred at room temperature for 18 hours. The mixture was cooled to 0° C. and acidified by addition of 2N hydrochloric acid dropwise to pH≈2-3. The mixture was allowed to warm to room temperature and the solvent removed in vacuo and azeotroped with toluene to dryness. The crude material was redissolved in dimethylformamide (3 mL). (S)-3,5-dichloro-4-(2-(3-(cyclopropylmethoxy)-4-(difluoromethoxy)phenyl)-2-hydroxyethyl)pyridine 1-oxide (161 mg, 0.38 mmol), 4-(dimethylamino)pyridine (20 mg, 0.16 mmol) followed by N-(3-dimethylaminopropyl)-N'-ethylcarbodiimide hydrochloride (123 mg, 0.64 mmol) were added, and reaction mixture was stirred at room temperature for 18 hours. The solvent was removed in vacuo and the residue was partitioned between EtOAc (50 mL) and water (50 mL) The organic phase was dried over MgSO$_4$, filtered and the solvent was removed in vacuo. The residue was purified twice by preparative HPLC to yield the title compound as white solid (40 mg, 13% yield over two steps).

$^1$H NMR (400 MHz, DMSO): δ 8.18 (s, 2H), 7.62 (d, J=7.8 Hz, 2H), 7.50 (t, J=6.5 Hz, 2H), 7.31 (t, J=7.6 Hz, 2H), 7.27-7.15 (m, 5H), 7.10 (s, 1H), 7.08 (t, J=75 Hz, 1H), 6.98 (d, J=8.4 Hz, 1H), 6.90 (d, J=7.7 Hz, 1H), 6.87-6.80 (m, 2H), 6.00-5.92 (m, 1H), 5.14 (s, 2H), 4.85 (s, 2H), 4.69-4.64 (m, 1H), 4.51-4.41 (m, 1H), 4.29-4.18 (m, 2H), 4.00-3.93 (m, 1H), 3.90 (d, J=6.9 Hz, 2H), 3.62-3.51 (m, 1H), 3.47 (dd, J=15.1, 9.4 Hz, 1H), 3.41-3.27 (m, 3H), 3.26-3.17 (m, 1H), 3.12 (dd, J=14.3, 7.9 Hz, 1H), 2.66-2.58 (m, 2H), 1.86 (s, 1H), 1.59-1.53 (m, 1H), 1.51-1.45 (m, 1H), 1.32-1.28 (m, 1H), 1.29-1.13 (m, 2H), 0.56 (d, J=7.5 Hz, 2H), 0.38-0.31 (m, 2H). LCMS (Method 1): [MH+]=971 at 3.09 min.

The following compound was synthesized in a similar way to Example 1, starting from Intermediate 8 above described.

| Structure | Example | Analytical Data |
|---|---|---|
| [(1S)-1-[3-(cyclopropylmethoxy)-4-(difluoromethoxy)phenyl]-2-(3,5-dichloro-1-oxido-pyridin-1-ium-4-yl)ethyl] 1-[4-[[4-[(N-[(3R)-quinuclidin-3-yl]oxycarbonylanilino)methyl]phenoxy]-methyl]benzoyl]azetidine-3-carboxylate 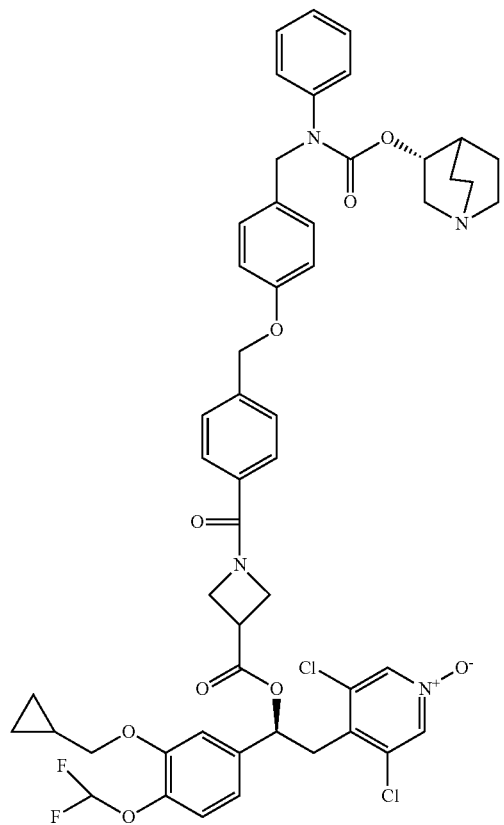 [SMILES: O=C(O[C@@H](Cc1c(Cl)c[n+]([O-])cc1Cl)c1ccc(OC(F)F)c(OCC2CC2)c1)C1CN(C(=O)c2ccc(COc3ccc(CN(C(=O)O[C@H]4CN5CCC4CC5)c4ccccc4)cc3)cc2)C1] | Example 2 | $^1$H NMR (400 MHz, DMSO): δ 8.55 (s, 2 H), 7.61 (d, J = 7.9 Hz, 2 H), 7.50 (t, J = 5.7 Hz, 2 H), 7.32 (t, J = 7.6 Hz, 2 H), 7.25 (d, J = 7.4 Hz, 2 H), 7.24-7.12 (m, 4 H), 7.09 (d, J = 2.0 Hz, 1 H), 7.07 (t, J = 75 Hz, 1 H), 6.99-6.90 (m, 3 H), 6.00-5.89 (m, 1 H), 5.12 (s, 2 H), 4.99-4.85 (m, 1 H), 4.85 (d, J = 15.9 Hz, 1 H), 4.79 (d, J = 15.5 Hz, 1 H), 4.48-4.39 (m, 1 H), 4.28-4.17 (m, 2 H), 4.00-3.92 (m, 1 H), 3.89 (d, J = 7.0 Hz, 2 H), 3.68-3.60 (m, 1 H), 3.51-3.50 (m, 1 H), 3.46 (dd, J = 14.2, 9.5 Hz, 1 H), 3.29-3.07 (m, 5 H), 3.03-2.95 (m, 1 H), 2.19-2.08 (m, 1 H), 1.85-1.72 (m, 2 H), 1.66-1.39 (m, 2 H), 1.25-1.11 (m, 1 H), 0.63-0.47 (m, 2 H), 0.40-0.26 (m, 2 H). LCMS (Method 1): [MH+] = 971 at 3.12 min. |

Example 3

[(1S)-1-[3-(Cyclopropylmethoxy)-4-(difluoromethoxy)phenyl]-2-(3,5-dichloro-1-oxido-pyridin-1-ium-4-yl)ethyl](2S)-3-[3-[[3-[(N-[(3R)-quinuclidin-3-yl]oxycarbonylanilino)methyl]phenoxy]methyl]benzoyl]thiazolidine-2-carboxylate

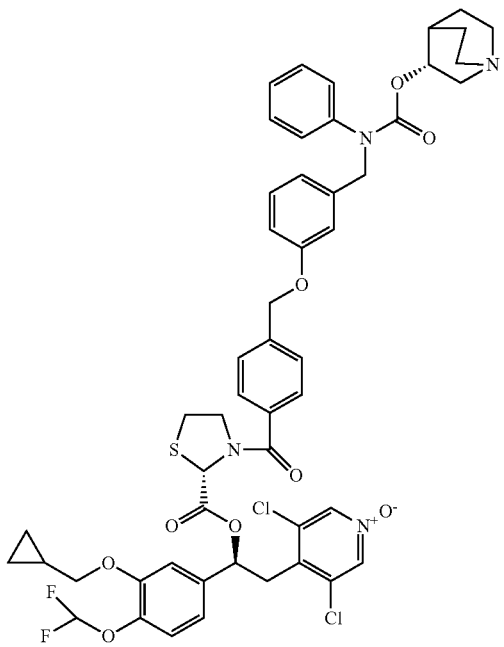

A solution of methyl 4-[[3-[(N-[(3R)-quinuclidin-3-yl]oxycarbonylanilino)-methyl]phenoxy]methyl]benzoate (Intermediate 5 above described) (419 mg, 0.84 mmol) in THF (2 mL) and methanol (2 mL) was added with an aqueous solution of 1N lithium hydroxide (1.7 mL, 1.68 mmol). The reaction was stirred at room temperature for 18 hours. The mixture was cooled to 0° C. and acidified by addition of 2 N hydrochloric acid dropwise to pH≈2-3. The mixture was allowed to warm to room temperature and the solvent removed in vacuo and azeotroped with toluene to dryness. This crude material was dissolved in DMF (5 mL) and ⅓ of the solution was used in the next step. [(1S)-1-[3-(cyclopropylmethoxy)-4-(difluoromethoxy)phenyl]-2-(3,5-dichloro-1-oxido-pyridin-1-ium-4-yl)ethyl](2S)-thiazolidine-2-carboxylate hydrochloride (Intermediate 9 above described) (142 mg, 0.25 mmol), 4-(dimethylamino)pyridine (13 mg, 0.11 mmol) followed by N-(3-dimethylaminopropyl)-N'-ethylcarbodiimide hydrochloride (81 mg, 0.42 mmol) were added and the reaction mixture was stirred at room temperature for 18 hours. Additional amounts of [(1S)-1-[3-(cyclopropylmethoxy)-4-(difluoromethoxy)-phenyl]-2-(3,5-dichloro-1-oxido-pyridin-1-ium-4-yl)ethyl](2S)-thiazolidine-2-carboxylate hydrochloride (140 mg, 0.25 mmol), N-(3-dimethylaminopropyl)-N'-ethylcarbodiimide hydrochloride (81 mg, 0.42 mmol) and 4-(dimethylamino)pyridine (13 mg, 0.11 mmol) were added to the reaction mixture and was stirred at room temperature for a further 18 hours. The solvent was removed in vacuo and the residue was partitioned between EtOAc (50 mL) and water. The organic phase was dried over MgSO$_4$, filtered and the solvent was removed in vacuo. The residue was purified by preparative HPLC to yield the title compound as white solid (16 mg, 8% yield over two steps).

$^1$H NMR (400 MHz, DMSO at 110° C.): δ 8.35 (s, 2H), 7.46 (d, J=8.0 Hz, 2H), 7.42 (d, J=8.1 Hz, 2H), 7.29 (d, J=7.9 Hz, 2H), 7.23-7.13 (m, 5H), 7.09 (d, J=2.2 Hz, 1H), 6.97 (dd, J=8.4, 3.4 Hz, 1H), 6.95 (t, J=75.3 Hz, 1H), 6.92-6.87 (m, 2H), 6.84 (d, J=7.7 Hz, 1H), 6.06 (dd, J=8.9, 5.3 Hz, 1H), 5.12 (s, 2H), 4.84 (s, 2H), 4.71-4.65 (m, 1H), 4.04-3.96 (m, 1H), 3.90 (d, J=6.7 Hz, 2H), 3.75 (dt, J=11.1, 6.2 Hz, 1H), 3.48 (dd, J=14.2, 8.8 Hz, 1H), 3.32 (dd, J=14.2, 5.4 Hz, 1H), 3.17-2.90 (m, 4H), 2.68-2.54 (m, 4H), 2.54-2.41 (m, 1H), 1.89-1.83 (m, 1H), 1.64-1.52 (m, 1H), 1.52-1.42 (m, 1H), 1.42-1.32 (m, 1H), 1.25-1.13 (m, 2H), 0.56-0.52 (m, 2H), 0.35-0.27 (m, 2H). LCMS (Method 1): [MH+]=1003 at 3.22 min.

The following compound was synthesized in a similar way to Example 3, starting from Intermediate 6 above described.

| Structure | Example | Analytical Data |
|---|---|---|
| [(1S)-1-[3-(cyclopropylmethoxy)-4-(difluoromethoxy)phenyl]-2-(3,5-dichloro-1-oxido-pyridin-1-ium-4-yl)ethyl] (2S)-3-[4-[[4-[(N-[(3R)-quinuclidin-3-yl]oxycarbonylanilino)methyl]phenoxy]-methyl]benzoyl]thiazolidine-2-carboxylate 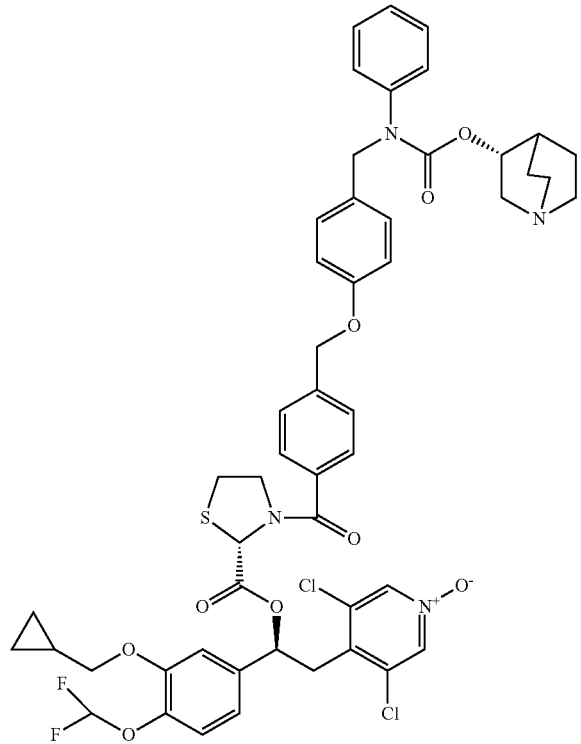 [SMILES: O=C(O[C@@H](Cc1c(Cl)c[n+]([O-])cc1Cl)c1ccc(OC(F)F)c(OCC2CC2)c1)[C@@H]1SCCN1C(=O)c1ccc(COc2ccc(CN(C(=O)O[C@H]3CN4CCC3CC4)c3ccccc3)cc2)cc1] | Example 4 | $^1$H NMR (400 MHz, DMSO at 110° C.): δ 8.35 (s, 2 H), 7.48 (d, J = 7.8 Hz, 2 H), 7.42 (d, J = 8.0 Hz, 2 H), 7.33-7.26 (m, 2 H), 7.20-7.13 (m, 6 H), 7.10 (d, J = 2.1 Hz, 1 H), 6.99-6.93 (m, 3 H), 6.95 (t, J = 75.3 Hz, 1 H), 6.06 (dd, J = 8.9, 5.3 Hz, 1 H), 5.13 (s, 2 H), 4.80 (s, 2 H), 4.70-4.65 (m, 1 H), 4.04-3.96 (m, 1 H), 3.92-3.87 (m, 2 H), 3.75 (dt, J = 11.1, 6.2 Hz, 1 H), 3.48 (dd, J = 14.2, 8.8 Hz, 1 H), 3.31 (dd, J = 14.2, 5.4 Hz, 1 H), 3.14-3.01 (m, 4 H), 2.68-2.55 (m, 4 H), 2.54-2.41 (m, 1 H), 1.88-1.84 (m, 1 H), 1.64-1.52 (m, 1 H), 1.51-1.34 (m, 2 H), 1.24-1.14 (m, 2 H), 0.57-0.51 (m, 2 H), 0.33-0.27 (m, 2 H). LCMS (Method 1): [MH+] = 1003 at 3.22 min. |

Example 5

[(1S)-1-[3-(Cyclopropylmethoxy)-4-(difluoromethoxy)phenyl]-2-(3,5-dichloro-1-oxido-pyridin-1-ium-4-yl)ethyl](2S)-3-[3-[2-[[3-[(N-[(3R)-quinuclidin-3-yl]oxycarbonylanilino)methyl]benzoyl]amino]ethylcarbamoyl]phenyl]sulfonylthiazolidine-2-carboxylate formate salt

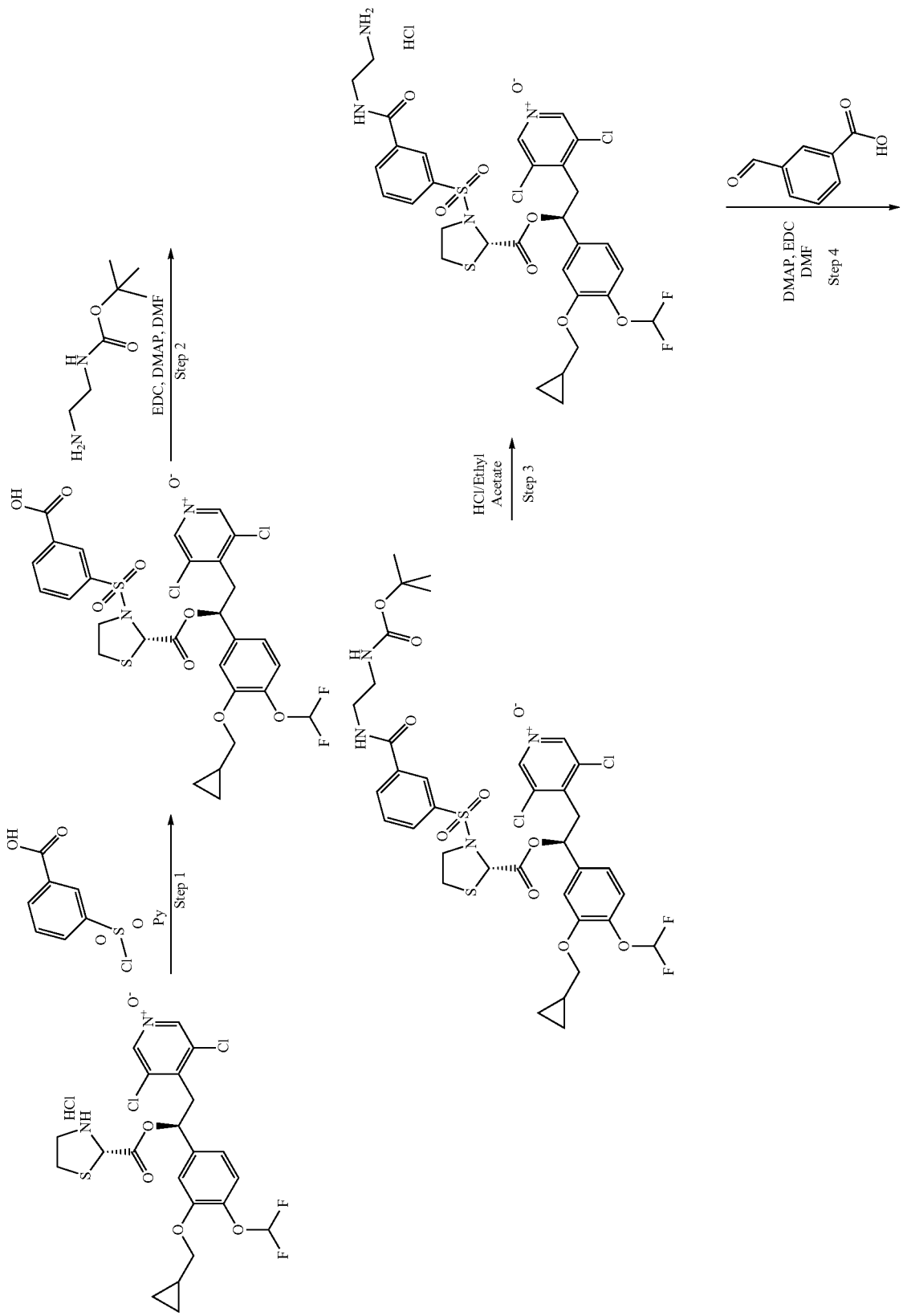

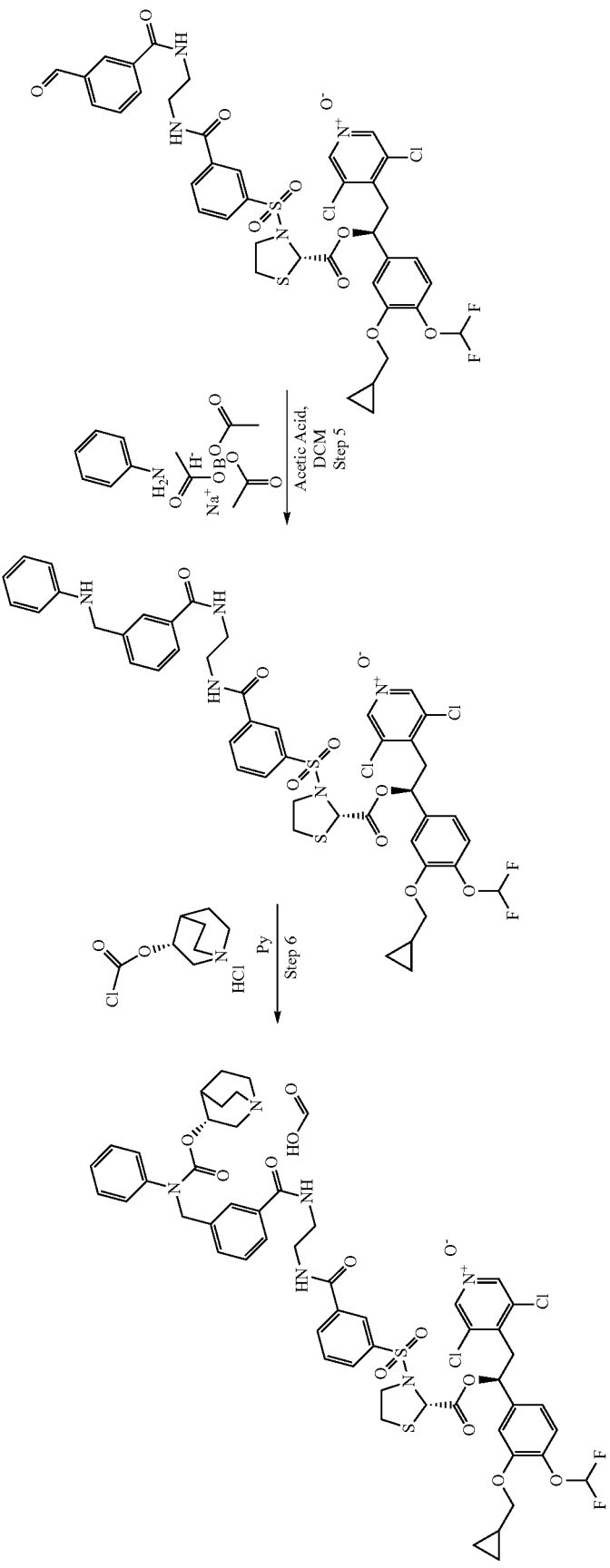

Step 1. 4-((S)-2-((S)-3-(3-Carboxyphenylsulfonyl) thiazolidine-2-carbonyloxy)-2-(3-(cyclopropylmethoxy)-4-(difluoromethoxy)phenyl)ethyl)-3,5-dichloropyridine 1-oxide 3,5-Dichloro-4-((S)-2-(3-(cyclopropylmethoxy)-4-(difluoromethoxy)phenyl)-2-(((S)-thiazolidine-2-carbonyl)oxy) ethyl)pyridine 1-oxide hydrochloride (Intermediate 9 above described) (400 mg, 0,699 mmol) was dissolved in Pyridine (2 ml). 3-(chlorosulfonyl)benzoic acid (463 mg, 2,098 mmol) was added at 0° C., and the reaction was warmed at room temperature for 4 hrs to achieve completion. The reaction mixture was quenched with HCl 1N, and the precipitate was washed with HCl 1N, dissolved in DCM and the organic phase was washed with HCl 1N, water and brine, dried over Na2SO4 and concentrated under vacuum to give 4-((S)-2-(((S)-3-((3-carboxyphenyl)sulfonyl)thiazolidine-2-carbonyl)oxy)-2-(3-(cyclopropylmethoxy)-4-(difluoromethoxy) phenyl)ethyl)-3,5-dichloropyridine 1-oxide (352 mg, 0.490 mmol, 70% yield).

MS/ESI$^+$ 719.04 [MH]$^+$

Step 2. 4-((S)-2-((S)-3-(3-(2-(tert-Butoxycarbonylamino)ethylcarbamoyl)-phenylsulfonyl)thiazolidine-2-carbonyloxy)-2-(3-(cyclopropylmethoxy)-4-(difluoromethoxy)phenyl)ethyl)-3,5-dichloropyridine 1-oxide 4-((S)-2-((S)-3-(3-Carboxyphenylsulfonyl)thiazolidine-2-carbonyloxy)-2-(3-(cyclopropylmethoxy)-4-(difluoromethoxy)phenyl)ethyl)-3,5-dichloropyridine 1-oxide (200 mg, 0.278 mmol), tert-butyl 2-aminoethylcarbamate (89 mg, 0.556 mmol), DMAP (40.7 mg, 0.334 mmol) and EDC (160 mg, 0.834 mmol) were dissolved in DMF. The reaction was stirred at room temperature overnight to achieve completion. The reaction mixture was diluted with water, and the precipitate was washed with water, dissolved in ethyl acetate and extracted with HCl 1N, NaHCO3 5% and brine. The organic phase was dried over Na2SO4 and concentrated under vacuum to give 4-((S)-2-((S)-3-(3-(2-(tert-butoxycarbonylamino)ethylcarbamoyl)phenylsulfonyl)thiazolidine-2-carbonyloxy)-2-(3-(cyclopropylmethoxy)-4-(difluoromethoxy) phenyl)ethyl)-3,5-dichloropyridine 1-oxide (211 mg, 0.245 mmol, 88% yield).

MS/ESI$^+$ 861.16 [MH]$^+$

Step 3. 4-((S)-2-((S)-3-(3-(2-Aminoethylcarbamoyl) phenylsulfonyl)-thiazolidine-2-carbonyloxy)-2-(3-(cyclopropylmethoxy)-4-(difluoromethoxy)phenyl) ethyl)-3,5-dichloropyridine 1-oxide hydrochloride 4-((S)-2-((S)-3-(3-(2-(tert-Butoxycarbonylamino)ethylcarbamoyl)phenylsulfonyl)-thiazolidine-2-carbonyloxy)-2-(3-(cyclopropylmethoxy)-4-(difluoromethoxy)phenyl)-ethyl)-3,5-dichloropyridine 1-oxide (211 mg, 0.245 mmol) was dissolved in HCl 1N in Ethyl Acetate (5 ml, 165 mmol). The reaction was stirred at room temperature for 5 hrs to achieve completion. The reaction mixture was concentrated under vacuum, and the crude product was triturated with Et2O and filtered to give the crude 4-((S)-2-((S)-3-(3-(2-aminoethylcarbamoyl)phenylsulfonyl)thiazolidine-2-carbonyloxy)-2-(3-(cyclopropylmethoxy)-4-(difluoromethoxy) phenyl)ethyl)-3,5-dichloropyridine 1-oxide hydrochloride (195 mg, 0.245 mmol, 100% yield).

MS/ESI$^+$ 761.1 [MH]$^+$

Step 4. 3,5-Dichloro-4-((S)-2-(3-(cyclopropylmethoxy)-4-(difluoromethoxy)-phenyl)-2-((S)-3-(3-(2-(3-formylbenzamido)ethylcarbamoyl)phenylsulfonyl)-thiazolidine-2-carbonyloxy)ethyl)pyridine 1-oxide 4-((S)-2-((S)-3-(3-(2-Aminoethylcarbamoyl)phenylsulfonyl)thiazolidine-2-carbonyloxy)-2-(3-(cyclopropylmethoxy)-4-(difluoromethoxy)phenyl)ethyl)-3,5-dichloropyridine 1-oxide hydrochloride (195 mg, 0.244 mmol), 3-formylbenzoic acid (110 mg, 0.733 mmol), DMAP (5.97 mg, 0.049 mmol) and EDC (141 mg, 0.733 mmol) were dissolved in DMF. The reaction was stirred at RT overnight to achieve completion. The reaction mixture was diluted with water, and the precipitate was washed with water, dissolved in DCM and extracted with water. The organic phase was dried over Na2SO4 and concentrated under vacuum to give 3,5-dichloro-4-((S)-2-(3-(cyclopropylmethoxy)-4-(difluoromethoxy)phenyl)-2-((S)-3-(3-(2-(3-formylbenzamido) ethylcarbamoyl)-phenylsulfonyl)thiazolidine-2-carbonyloxy)ethyl)pyridine 1-oxide (100 mg, 0.112 mmol, 45.8% yield).

MS/ESI$^+$ 893.1 [MH]$^+$

Step 5. 3,5-Dichloro-4-((S)-2-(3-(cyclopropylmethoxy)-4-(difluoromethoxy)phenyl)-2-(((S)-3-((3-((2-(3-((phenylamino)methyl)benzamido)-ethyl) carbamoyl)phenyl)sulfonyl)-thiazolidine-2-carbonyl) oxy)ethyl)pyridine 1-oxide 3,5-Dichloro-4-((S)-2-(3-(cyclopropylmethoxy)-4-(difluoromethoxy)phenyl)-2-(((S)-3-((3-((2-(3-formylbenzamido)ethyl)carbamoyl)phenyl)sulfonyl)thiazolidine-2-carbonyl)oxy)ethyl)pyridine 1-oxide (30 mg, 0.034 mmol) was dissolved in DCM (300 μl, 4.66 mmol). Aniline (3.75 mg, 0.040 mmol) and acetic Acid (2.306 μl, 0.040 mmol) were added, and the mixture was stirred at RT for 30'. Sodium triacetoxyborohydride (8.54 mg, 0.040 mmol) was added, and the mixture was stirred at room temperature for 8 hrs to achieve completion. The reaction mixture was diluted with DCM and extracted with water. The organic phase was dried over Na2SO4 and concentrated under vacuum to give 3,5-dichloro-4-((S)-2-(3-(cyclopropylmethoxy)-4-(difluoromethoxy)phenyl)-2-(((S)-3-((3-((2-(3-((phenylamino)methyl)benzamido)ethyl)carbamoyl)phenyl)-sulfonyl) thiazolidine-2-carbonyl)oxy)ethyl)pyridine 1-oxide (35 mg, 0.036 mmol, 107% yield).

MS/ESI$^+$ 970.2 [MH]$^+$

Step 6. [(1S)-1-[3-(Cyclopropylmethoxy)-4-(difluoromethoxy)phenyl]-2-(3,5-dichloro-1-oxido-pyridin-1-ium-4-yl)ethyl](2S)-3-[3-[2-[[3-[(N-[(3R)-quinuclidin-3-yl]oxycarbonylanilino)methyl]benzoyl]amino]ethylcarbamoyl]phenyl]sulfonylthiazolidine-2-carboxylate formate salt

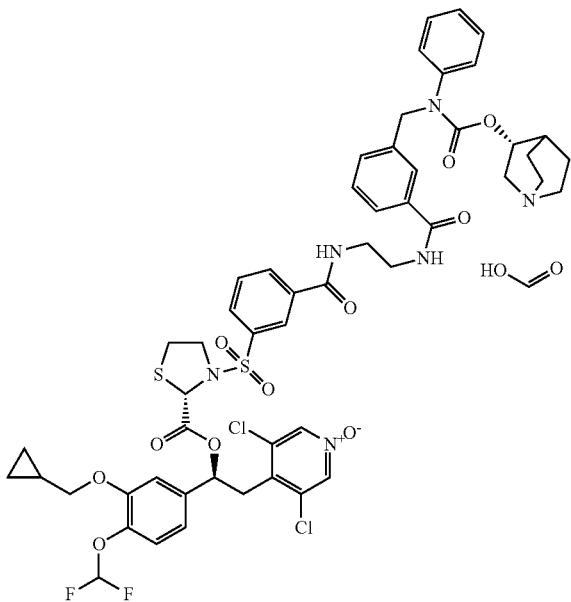

3,5-Dichloro-4-((S)-2-(3-(cyclopropylmethoxy)-4-(difluoromethoxy)phenyl)-2-((S)-3-(3-(2-(3-((phenylamino)methyl)benzamido)ethylcarbamoyl)phenylsulfonyl)-thiazolidine-2-carbonyloxy)ethyl)pyridine 1-oxide (35 mg, 0.036 mmol) was dissolved in pyridine (2 ml). (R)-quinuclidin-3-yl carbonochloridate hydrochloride (described in the co-pending International Patent Application No. PCT/EP2013/075529 (published as WO 2104/086855) (8.15 mg, 0.036 mmol) was added, and the reaction was stirred at room temperature for 6 hrs to achieve completion. The reaction mixture was diluted with HCl 1N and extracted with ethyl acetate. The organic phase was washed with water, brine, dried over Na2SO4 and concentrated under vacuum. The crude was purified by preparative HPLC to give 3,5-dichloro-4-((S)-2-(3-(cyclopropylmethoxy)-4-(difluoromethoxy)phenyl)-2-(((S)-3-((3-((2-(3-((phenyl(((R)-quinuclidin-3 yloxy)carbonyl)amino)methyl)benzamido)ethyl)carbamoyl)-phenyl)sulfonyl)thiazolidine-2-carbonyl)oxy)ethyl)pyridine 1-oxide formate (12.65 mg, 10.81 μmol, 30% yield).

MS/ESI$^+$ 1123.3 [MH]$^+$ $^1$H NMR (400 MHz, DMSO-d$_6$) δ ppm 8.94 (t, 1H), 8.62 (t, 1H), 8.59 (s, 2H), 8.31 (s, 1H), 8.25 (s, 1H), 8.19 (d, J=7.94 Hz, 1H), 8.03 (d, J=7.94 Hz, 1H), 7.66-7.80 (m, 3H), 7.22-7.46 (m, 5H), 7.15-7.20 (m, 2H), 7.11 (d, J=1.76 Hz, 1H), 7.08 (t, J=75.00 Hz, 1H), 6.95 (dd, J=8.38, 1.76 Hz, 1H), 6.01 (dd, J=9.04, 5.07 Hz, 1H), 5.48 (s, 1H), 4.92 (s, 2H), 4.61-4.70 (m, 1H), 3.90 (d, J=6.62 Hz, 2H), 3.79 (m, 1H), 3.68 (m, 1H), 3.41-3.53 (m, 6H), 3.06 (m, 2H), 2.93 (m, 2H), 2.52-2.70 (m, 4H), 2.46 (m, 1H), 1.55-1.40 (m, 4H), 1.39-1.60 (m, 1H), 0.56 (dd, J=8.16, 1.54 Hz, 2H), 0.32 (d, J=5.29 Hz, 2H)

Example 6

[(1S)-1-[3-(Cyclopropylmethoxy)-4-(difluoromethoxy)phenyl]-2-(3,5-dichloro-1-oxido-pyridin-1-ium-4-yl)ethyl](2S)-3-[3-[[3-[(2-fluoro-N-[(3R)-quinuclidin-3-yl]oxycarbonyl-anilino)methyl]benzoyl]oxymethyl]phenyl]sulfonylthiazolidine-2-carboxylate formate salt

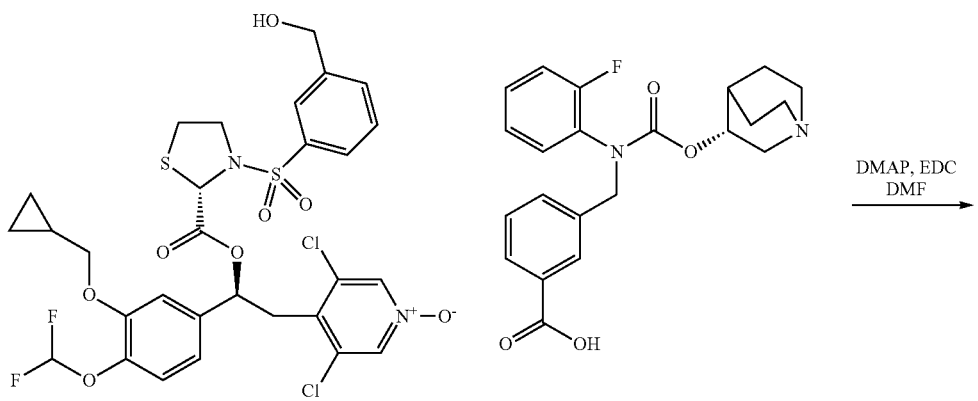

-continued

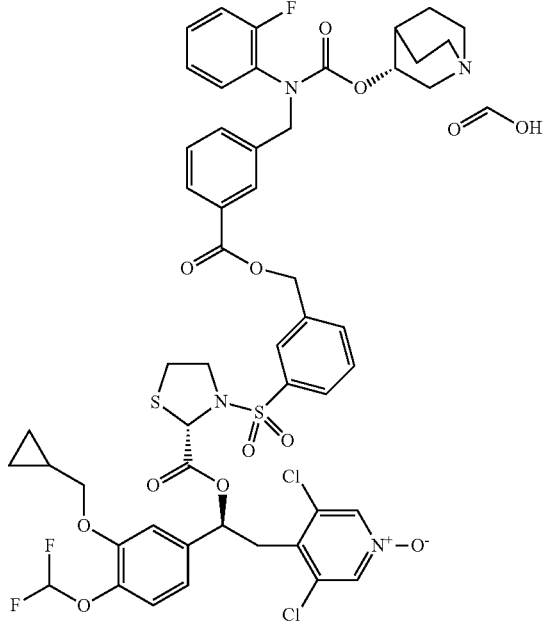

3,5-Dichloro-4-((S)-2-(3-(cyclopropylmethoxy)-4-(difluoromethoxy)phenyl)-2-(((S)-3-((3-(hydroxymethyl)phenyl)sulfonyl)thiazolidine-2-carbonyl)oxy)ethyl)pyridine 1-oxide (described in WO 2012/168226, which is incorporated herein by reference in its entirety, Example 25) (50 mg, 0.071 mmol), DMAP (17.31 mg, 0.142 mmol), EDC (67.9 mg, 0.354 mmol) and (R)-3-(((2-fluorophenyl)((quinuclidin-3-yloxy)carbonyl)amino)-methyl)benzoic acid (prepared from the corresponding ester, described in the co-pending International Patent Application No. PCT/EP2013/075526 (published as WO 2014/086852), which is incorporated herein by reference in its entirety, following the procedure reported for Example 1 of the above-mentioned application) (56.5 mg, 0.142 mmol) were dissolved in DMF (2 ml). The reaction was stirred at RT for 24 hrs to achieve completion.

The reaction mixture was diluted with water, and the precipitate was filtered and washed with water, dissolved in DCM and extracted with water and brine. The organic phase was dried over Na2SO4 and concentrated under vacuum. The crude was purified by preparative HPLC to give 3,5-dichloro-4-((S)-2-(3-(cyclopropylmethoxy)-4-(difluoromethoxy)phenyl)-2-(((S)-3-((3-(((3-(((2-fluorophenyl)(((R)-quinuclidin-3-yloxy)carbonyl)amino)methyl)benzoyl)oxy)methyl)phenyl)sulfonyl)thiazolidine-2-carbonyl)oxy)ethyl)pyridine 1-oxide formate (15 mg, 0.013 mmol, 18.70% yield).

MS/ESI$^+$ 1185.22 [MH]$^+$ $^1$H NMR (400 MHz, DMSO-d$_6$) δ ppm 8.56 (s, 2H), 7.95-8.04 (m, 1H), 7.75-7.93 (m, 4H), 7.64-7.72 (m, 1H), 7.42-7.58 (m, 2H), 7.00-7.39 (m, 7H), 6.82-6.98 (m, 2H), 5.94-6.05 (m, 1H), 5.35-5.51 (m, 3H), 4.71-4.98 (m, 3H), 3.87-3.98 (m, 2H), 3.73-3.84 (m, 1H), 3.53-3.70 (m, 2H), 3.36-3.50 (m, 1H), 2.89-3.00 (m, 1H), 2.73-2.87 (m, 2H), 2.56-2.68 (m, 2H), 1.58-1.90 (m, 5H), 1.30-1.40 (m, 4H), 1.14-1.23 (m, 2H), 0.47-0.65 (m, 2H), 0.24-0.40 (m, 2H).

Pharmacological Activity of the Compounds of the Invention.
In Vitro Determination of PDE4 Inhibitory Activity.

In vitro determination of PDE4 inhibitory activity for compounds of the invention may be determined according to one of the protocols reported below.

PDE4B2 HTRF Assay:

PDE4B2 activity is detected using the LANCE Ultra cAMP homogeneous time resolved fluorescence resonance energy transfer (TR-FRET) assay from Perkin Elmer. The assay is based on the competition between the europium (Eu) chelate-labeled cAMP tracer and sample cAMP for binding sites on cAMP-specific monoclonal antibodies (mAb) labelled with the ULight™ dye. The assay is carried out in 384-well low volume plates in a volume of 10 μl. Human recombinant PDE4B2 (80 pM) is incubated for 2 h with 3 nM cAMP in buffer containing 1×HBSS, 5 mM HEPES, 3 mM MgCl$_2$, 0.1% BSA, pH 7.4 with or without test compounds. The enzymatic reactions are efficiently stopped by the addition of 500 μM IBMX present in the combined Stop/Detection buffer containing europium (Eu) chelate-labeled cAMP tracer and cAMP-specific monoclonal antibodies (mAb) labelled with the ULight™ dye. Samples are then further incubated for 1 h before plates are read at ex 340 nm and em at 665 nm and 615 nm on an EnVision reader. IC$_{50}$ values are determined from competition curves using a non-linear curve fitting program.

PDE4 Cell Free Assay Protocol:

PDE4 activity is determined in U937 human monocytic supernatants cells lysate. Cells are cultured, harvested and supernatant fraction prepared essentially as described in Torphy T J et al J. Pharmacol. Exp. Ther. 1992; 263:1195-1205, which is incorporated herein by reference in its entirety. U937 cells are grown at 37° C., 5% CO$_2$ in RPMI 1640 with GlutaMAX™-I medium supplemented with 10% fetal bovine serum and 100 μg/mL Pen-strep (Gibco). Cells are harvested and washed twice by centrifugation (150×g, 8 min) in cold PBS. Washed cells are re-suspended in cold Krebs-Ringer-Henseleit buffer at a final concentration 20×10$^6$ cells/mL and sonicated. After centrifugation at 15000×g for 20 min, the supernatants are pooled, divided in aliquots and stored at −80° C. PDE4 activity is determined in cells supernatants by assaying cAMP disappearance from the incubation mixtures.

The concentration of the test compounds ranges between 10$^{-12}$ M and 10$^{-6}$ M. Reactions are stopped by enzyme heat inactivation (2.5 minutes at 100° C.) and residual cAMP content is determined using the 'LANCE cAMP Assay' from PerkinElmer following the provider instructions.

The results, expressed as mean±standard deviation of the molar concentration of the test compound producing 50% inhibition of cAMP disappearance ($IC_{50}$). Percentage of inhibition of PDE4 activity is calculated, assuming cAMP disappearance in the absence of inhibitors as 100% and cAMP disappearance in heat inactivated samples as 0%.

Representative compounds of the invention, when tested in one of the above reported protocols, displayed an $IC_{50}$ lower than 100 nM.

In Vitro Determination of M3 Antagonism.

In vitro determination of M3 antagonism for compounds of the invention may be determined according to one of the protocols reported below, M3 Receptor Radioligand Binding Assay:

Human $M_3$ receptor membranes (15 μg/well) from Perkin Elmer are incubated with 0.52 nM Scopolamine Methyl Chloride, [N-methyl-3H] with or without test compounds, or a saturating concentration of atropine (5 μM) for the determination of non-specific binding. The assay is carried out in 96-well polypropylene plates in a volume of 250 μl. The assay buffer used is 50 mM Tris-HCl, 154 mM NaCl (pH 7.4). The final assay concentration of DMSO is 0.5% (v/v). The plates are sealed and incubated for 2 h at room temperature on an orbital shaker (slow speed). Membranes are harvested onto 96-well unifilter GF/C filter plates pre-treated with 0.5% polyethyleneimine (v/v), using a filter manifold, washed four times with 200 μl of assay buffer. The plates are dried before addition of 50 μl of microscint-0, sealed then read in a Trilux Microbeta scintillation counter. $IC_{50}$ values are determined from competition curves using a non-linear curve fitting program. $K_i$ values are calculated from $IC_{50}$ values by the Cheng and Prusoff equation.

M3 Binding Assay:

CHO-K1 clone cells expressing the human M3-receptor (Swissprot P20309) were harvested in $Ca^{++}/Mg^{++}$ free phosphate-buffered saline and collected by centrifugation at 1500 rpm for 3 min. The pellets were resuspended in ice cold buffer A (15 mM Tris-HCl pH 7.4, 2 mM $MgCl_2$, 0.3 mM EDTA, 1 mM EGTA) and homogenized by a PBI politron (setting 5 for 15 s). The crude membrane fraction was collected by two consecutive centrifugation steps at 40000 g for 20 min at 4° C., separated by a washing step in buffer A. The pellets obtained were finally resuspended in buffer B (75 mM Tris HCl pH 7.4, 12.5 mM $MgCl_2$, 0.3 mM EDTA, 1 mM EGTA, 250 mM sucrose), and aliquots were stored at −80° C.

The day of experiment, frozen membranes were resuspended in buffer C (50 mM Tris-HCl pH 7.4, 2.5 mM $MgCl_2$, 1 mM EDTA). The non-selective muscarinic radioligand [$^3$H]-N-methyl scopolamine (*Mol. Pharmacol.* 45:899-907, which is incorporated herein by reference in its entirety) was used to label the M3 binding sites. Binding experiments were performed in duplicate (ten point concentrations curves) in 96 well plates at radioligand concentration of 0.1-0.3 nM. The non-specific binding was determined in the presence of cold N-methyl scopolamine 10 μM. Samples (final volume 0.75 mL) were incubated at room temperature for 90 min. The reaction was terminated by rapid filtration through GF/B Unifilter plates and two washes (0.75 mL) with cold buffer C using a Packard Filtermate Harvester. Radioactivity on the filters was measured by a microplate scintillation counter TriCarb 2500 (PerkinElmer).

Representative compounds of the invention, when tested in one of the above reported protocols, displayed an $IC_{50}$ lower than 100 nM.

Representative compounds of the invention displayed an $IC_{50}$ lower than 100 nM in both PDE4 cell free and M3 binding assays.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

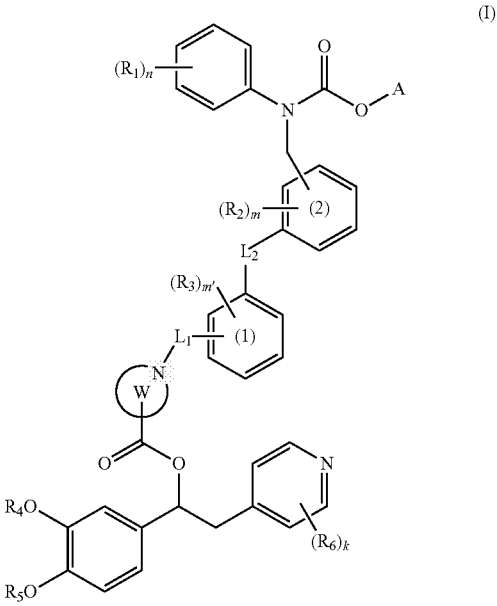

wherein:
each $R_1$ is the same or different and is independently hydrogen, halogen, ($C_1$-$C_4$) alkyl, ($C_1$-$C_4$) alkoxy, ($C_1$-$C_4$) haloalkyl, hydroxy, —$SO_2NR^IR^{II}$, —CN, —N($R^I$)$SO_2R^{III}$, —$NR^IR^{II}$, —C(O)$NR^IR^{II}$, or —N($R^I$)C(O)$R^{III}$, and wherein each said ($C_1$-$C_4$) alkyl is optionally substituted by one or more groups selected from the group consisting of ($C_3$-$C_7$) cycloalkyl, hydroxyl, and —$NR^IR^{II}$ and wherein each said ($C_1$-$C_4$) alkoxy is optionally substituted by one or more halogen atoms or ($C_3$-$C_7$) cycloalkyl groups, and wherein:
$R^I$ is hydrogen or ($C_1$-$C_6$) alkyl;
$R^{II}$ is hydrogen or ($C_1$-$C_6$) alkyl;
$R^{III}$ is hydrogen or ($C_1$-$C_6$) alkyl;
n is an integer ranging from 1 to 3;
each $R_2$ and each $R_3$ is the same or different and is hydrogen, halogen, ($C_1$-$C_4$) alkyl, ($C_1$-$C_4$) alkoxy, ($C_1$-$C_4$) haloalkyl, hydroxy, —$SO_2NR^IR^{II}$, —CN, —N($R^I$)$SO_2R^{III}$, —$NR^IR^{II}$, —C(O)$NR^IR^{II}$, or —N($R^I$)C(O)$R^{III}$ and wherein each said ($C_1$-$C_4$) alkyl is optionally substituted by one or more groups selected from the group consisting of ($C_3$-$C_7$) cycloalkyl, hydroxyl, and —$NR^IR^{II}$ and wherein each said ($C_1$-$C_4$) alkoxy is optionally substituted by one or more halogen atoms or $(C_3-C_7)$ cycloalkyl groups and wherein:

$R^I$, $R^{II}$, and $R^{III}$ are as defined above;

m and m' are the same of different and are independently an integer ranging from 1 to 3;

each $R_4$ and each $R_5$ is the same or different and is independently:

H;

$(C_3-C_7)$ cycloalkylcarbonyl;

$(C_1-C_6)$ alkyl, optionally substituted by one or more substituents selected from $(C_3-C_7)$ cycloalkyl and $(C_5-C_7)$ cycloalkenyl;

$(C_1-C_6)$ haloalkyl;

$(C_3-C_7)$ cycloalkyl;

$(C_5-C_7)$ cycloalkenyl;

$(C_2-C_6)$ alkenyl; or $(C_2-C_6)$ alkynyl;

or $R_4$ and $R_5$ together with the interconnecting atoms, form a 2,2-difluoro-1,3-dioxolane ring of formula (r) fused to the phenyl moiety which bears groups —$OR_4$ and —$OR_5$, wherein asterisks indicate carbon atoms shared with such phenyl ring:

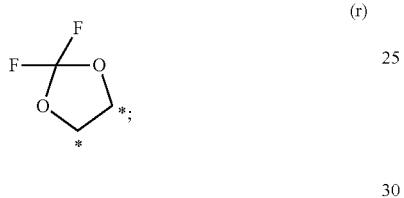

(r)

each $R_6$ is the same or different and is CN, $NO_2$, $CF_3$ or a halogen atom;

k is 0 or an integer ranging from 1 to 3;

$L_1$ is a bond, —C(O)—, —$SO_2$—, or —$(CH_2)$—;

the group

is a divalent saturated monocyclic heterocycloalkylene, which contains at least one nitrogen atom, and which is linked to the $L_1$ residue by one of its nitrogen atom;

$L_2$ is:

a bond;

$[1]-(CH_2)_q-[2]$;

$[1]-C(O)NH—(CH_2)_q—NH—C(O)-[2]$;

$[1]-C(O)O—(CH_2)_q—O—C(O)-[2]$;

$[1]-(CH_2)_qO-[2]$;

$[1]-O(CH_2)_q-[2]$;

$[1]-(CH_2)_q—O—C(O)-[2]$;

$[1]-C(O)O—(CH_2)_q[2]$-;

$[1]-(CH_2)_q—NH—C(O)-[2]$; or $[1]-C(O)NH—(CH_2)_q[2]$-;

wherein q is an integer ranging from 1 to 4; and wherein [1] and [2] represent, respectively, the point of attachment of group $L_2$ to a carbon atom of the phenylene ring (1) and to a carbon atom of the phenylene ring (2); and A is a nitrogen containing group which is:

a group (a) which is —$(CH_2)_s$—$NR_8R_9$ wherein s is an integer ranging from 1 to 4 and $R_8$ and $R_9$ are independently hydrogen or $(C_1-C_4)$ alkyl; and a group (b) which is a saturated monocyclic, bicyclic, or tricyclic heterocyclic ring system optionally substituted by one or two groups $R_{10}$ which are at each occurrence independently $(C_1-C_4)$ alkyl or benzyl, an N-oxide on the pyridine ring, a deuterated derivative, or a pharmaceutically acceptable salt thereof.

2. A compound, N-oxide, deuterated derivative, or pharmaceutically acceptable salt according to claim 1, which is represented by formula (IB):

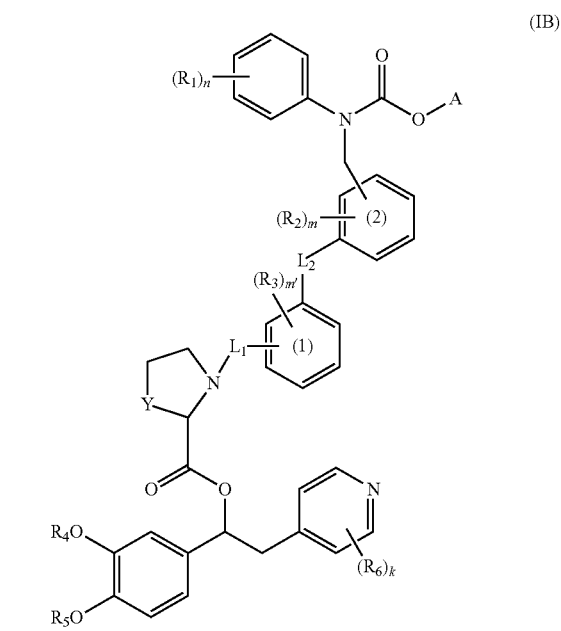

(IB)

wherein:

Y is —(CH2)-, —S—, or —N(H)—; and $L_1$ is —CO— or —$SO_2$—.

3. A compound, N-oxide, deuterated derivative, or pharmaceutically acceptable salt according to claim 1, which is represented by formula (IC)

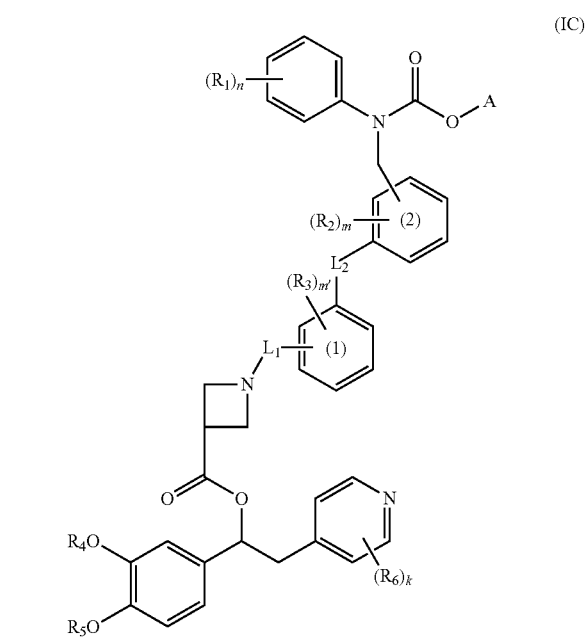

(IC)

wherein:

$L_1$ is —CO— or —$SO_2$—.-

4. A compound, N-oxide, deuterated derivative, or pharmaceutically acceptable salt according to claim 1, which is an N-oxide represented by formula (IA):

(IA)

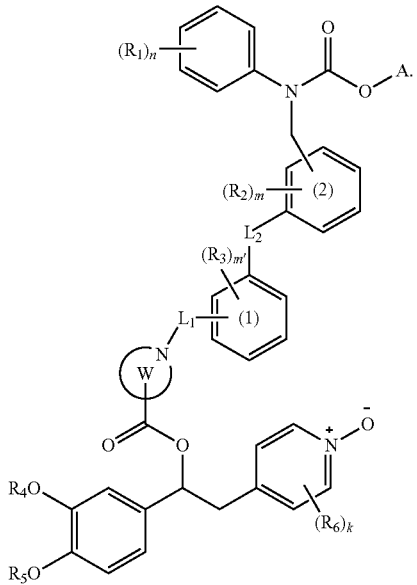

5. A compound, N-oxide, deuterated derivative, or pharmaceutically acceptable salt according to claim 1, which is represented by formula (I)' wherein the absolute configuration of carbon (1) is as shown:

(I)'

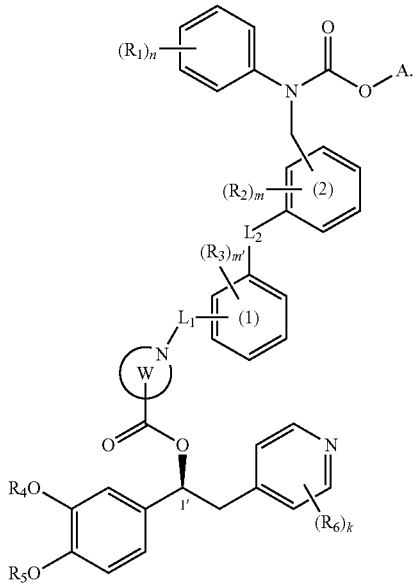

6. A compound, N-oxide, deuterated derivative, or pharmaceutically acceptable salt according to claim 1, which is a compound selected from the group consisting of:

[(1S)-1-[3-(cyclopropylmethoxy)-4-(difluoromethoxy)phenyl]-2-(3,5-dichloro-1-oxido-pyridin-1-ium-4-yl)ethyl](2S)-3-[3-[2-[[3-[(N-[(3R)-quinuclidin-3-yl]-oxycarbonylanilino)methyl]benzoyl]amino]ethylcarbamoyl]phenyl]sulfonylthiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-3-[3-[[3-[(2-fluoro-N-[(3R)-quinuclidin-3-yl]oxycarbonyl-anilino)methyl]benzoyl]oxymethyl]phenyl]sulfonylthiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-3-[4-[[4-[(N-[(3R)-quinuclidin-3-yl]oxycarbonylanilino)methyl]phenoxy]methyl]benzoyl]thiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-3-[4-[[3-[(N-[(3R)-quinuclidin-3-yl]oxycarbonylanilino)methyl]phenoxy]methyl]benzoyl]thiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl]1-[4-[[4-[(N-[(3R)-quinuclidin-3-yl]oxycarbonylanilino)methyl]phenoxy]methyl]benzoyl]azetidine-3-carboxylate; and

[(1S)-1-[3-(cyclopropylmethoxy)-4-(difluoromethoxy)phenyl]-2-(3,5-dichloro-1-oxido-pyridin-1-ium-4-yl)ethyl]1-[4-[[3-[(N-[(3R)-quinuclidin-3-yl]oxycarbonylanilino)methyl]phenoxy]methyl]benzoyl]azetidine-3-carboxylate, or a deuterated derivative or pharmaceutically acceptable salt of said compound.

7. A pharmaceutical composition, comprising a compound, N-oxide, deuterated derivative, or pharmaceutically acceptable salt according to claim 1 in admixture with one or more pharmaceutically acceptable carriers.

8. A pharmaceutical composition according to claim 7, further comprising another active ingredient.

9. A method for the treatment of asthma or COPD, said method comprising administering to a subject in need thereof an effective amount of a compound, N-oxide, deuterated derivative, or pharmaceutically acceptable salt according to claim 1.

10. An inhalation device, which contains a pharmaceutical composition according to claim 7.

11. An inhalation device, which contains a pharmaceutical composition according to claim 8.

12. A kit, comprising a pharmaceutical composition according to claim 7 and a device which is a single- or multi-dose dry powder inhaler, a metered dose inhaler or a nebulizer.

13. A kit, comprising a pharmaceutical composition according to claim 8 and a device which is a single- or multi-dose dry powder inhaler, a metered dose inhaler or a nebulizer.

* * * * *